US011633308B2

(12) United States Patent
Minoguchi et al.

(10) Patent No.: US 11,633,308 B2
(45) Date of Patent: *Apr. 25, 2023

(54) DISPOSABLE ABSORBENT ARTICLES AND ARRAYS OF SAID ARTICLES COMPRISING VISUAL CHARACTERISTICS

(71) Applicant: The Procter & Gamble Company, Cincinnati, OH (US)

(72) Inventors: Ryo Minoguchi, Cincinnati, OH (US); Sion Agami, Mason, OH (US); Vanessa Marie Melendez, Cincinnati, OH (US)

(73) Assignee: THE PROCTER & GAMBLE COMPANY, Cincinnati, OH (US)

( * ) Notice: Subject to any disclaimer, the term of this patent is extended or adjusted under 35 U.S.C. 154(b) by 532 days.

This patent is subject to a terminal disclaimer.

(21) Appl. No.: 16/692,331

(22) Filed: Nov. 22, 2019

(65) Prior Publication Data
US 2020/0093654 A1    Mar. 26, 2020

Related U.S. Application Data

(63) Continuation of application No. 15/074,258, filed on Mar. 18, 2016, now Pat. No. 10,548,781.

(60) Provisional application No. 62/136,003, filed on Mar. 20, 2015.

(51) Int. Cl.
| A61F 13/49 | (2006.01) |
| A61F 13/84 | (2006.01) |
| A61F 13/514 | (2006.01) |
| A61F 13/496 | (2006.01) |
| A61F 13/551 | (2006.01) |

(52) U.S. Cl.
CPC ...... *A61F 13/49009* (2013.01); *A61F 13/496* (2013.01); *A61F 13/51496* (2013.01); *A61F 13/84* (2013.01); *A61F 13/55145* (2013.01); *A61F 2013/8497* (2013.01)

(58) Field of Classification Search
CPC .............. A61F 13/49009; A61F 13/496; A61F 13/51496; A61F 13/55145; A61F 13/84; A61F 2013/8497
See application file for complete search history.

(56) References Cited

U.S. PATENT DOCUMENTS

| 5,158,819 | A | | 10/1992 | Goodman, Jr. et al. |
| 5,554,145 | A | * | 9/1996 | Roe ..................... A61F 13/4902 604/387 |
| 6,120,489 | A | * | 9/2000 | Johnson ............ A61F 13/15699 2/400 |
| 6,352,528 | B1 | * | 3/2002 | Weber ................... A61F 13/565 604/385.03 |
| 6,558,499 | B1 | | 5/2003 | Pargass et al. |

(Continued)

FOREIGN PATENT DOCUMENTS

| WO | 2006014853 A1 | 2/2006 |
| WO | WO-2013/159273 | 10/2013 |

OTHER PUBLICATIONS

All Office Actions, U.S. Appl. No. 15/074,258.
International Search Report and Written Opinion, PCT/US2016/022531, dated Jul. 5, 2016.

*Primary Examiner* — Michele M Kidwell
(74) *Attorney, Agent, or Firm* — William E. Gallagher; Richard L. Alexander

(57) ABSTRACT

An absorbent article or an array of absorbent articles comprising visual characteristics.

19 Claims, 13 Drawing Sheets

(56) References Cited

U.S. PATENT DOCUMENTS

| | | |
|---|---|---|
| 7,758,558 B2 | 7/2010 | Otsubo |
| 7,806,880 B2 | 10/2010 | Roe et al. |
| 9,517,168 B2 | 12/2016 | Trennepohl et al. |
| 10,548,781 B2 * | 2/2020 | Minoguchi ........... A61F 13/496 |
| 2004/0243083 A1 | 12/2004 | Matsuda |
| 2005/0131366 A1 | 6/2005 | Shimada |
| 2006/0020249 A1 | 1/2006 | Allen |
| 2006/0212010 A1 | 9/2006 | Roe |
| 2008/0065039 A1 | 3/2008 | Labit et al. |
| 2008/0132872 A1 | 6/2008 | Trennepohl |
| 2011/0106041 A1 | 5/2011 | Roe et al. |
| 2012/0173249 A1 | 7/2012 | Coenen et al. |
| 2013/0310798 A1 | 11/2013 | Glahn |
| 2014/0135729 A1 | 5/2014 | Roe et al. |

* cited by examiner

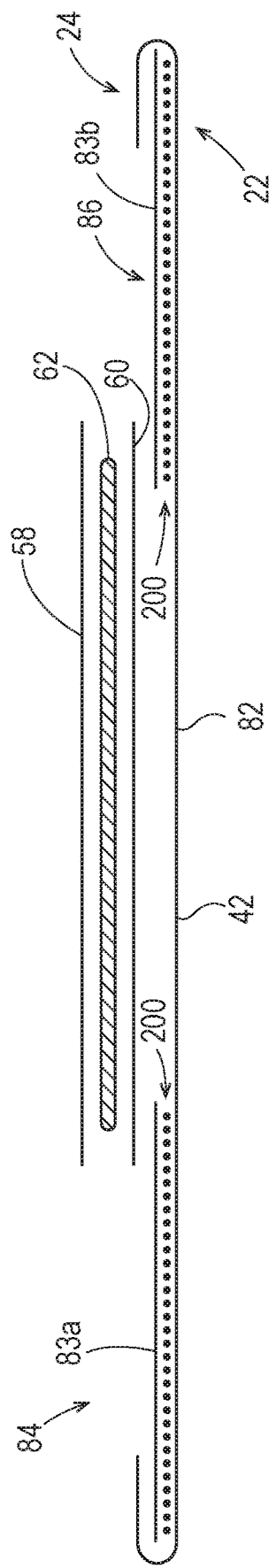

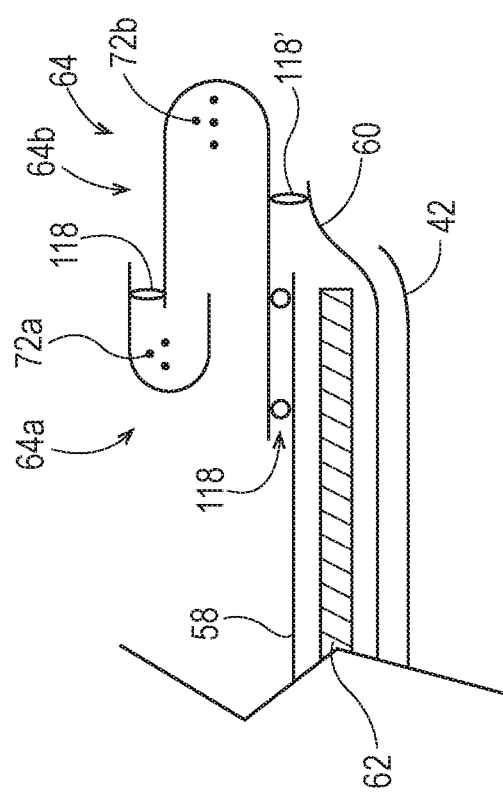

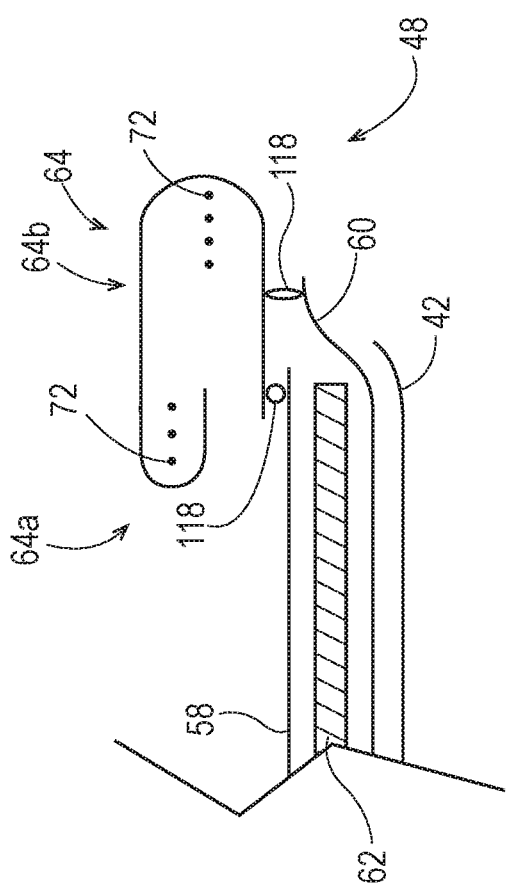

DISPOSABLE ABSORBENT ARTICLES AND ARRAYS OF SAID ARTICLES COMPRISING VISUAL CHARACTERISTICS

CROSS REFERENCE TO RELATED APPLICATIONS

This application is a continuation of, and claims priority under 35 U.S.C. § 120 to, U.S. patent application Ser. No. 15/074,258, filed on Mar. 18, 2016, which claims the benefit, under 35 USC § 119(e), of U.S. Provisional Patent Application No. 62/136,003, filed on Mar. 20, 2015, the entire disclosures of which are fully incorporated by reference herein.

FIELD

The present disclosure is directed to disposable absorbent articles and arrays of disposable absorbent articles which comprise one or more visual characteristics.

BACKGROUND

Adult incontinence ("AI") articles are designed to absorb and contain liquid and other discharges from the human body to prevent the body and clothing from becoming soiled. Some wearers prefer a pant style that provides the maximum coverage, fully covering the buttocks as well as rising up past and covering the belly button. Other wearers, however, especially younger wearers, prefer lower cut designs as these articles are typically more underwear like and less noticeable under clothing. The challenge, however, is to provide the desired level of leak protection, while providing an article with a smaller silhouette. Another challenge is to provide a line-up of AI articles that meets the needs and stylistic desires of diverse wearers, which can range over several hundred pounds. Beyond the nonwoven structure and elastic profiles of these articles, there is a need to communicate the fit and performance of the article. Thus, it is the combination of nonwovens/elastic structure and visual characteristics (including graphics) that makes for a complete article, that not only performs, but also signals to the wearer that the needed fit and performance can be/is being achieved. Thus, it is an object of the present disclosure to describe absorbent articles and arrays of absorbent articles designed to meet these needs.

BRIEF DESCRIPTION OF THE DRAWINGS

FIG. 4A-4C are schematic cross section views of suitable embodiments taken along line 4-4 in FIG. 3;

FIG. 5A-5C are schematic cross section views of suitable cuff embodiments taken along line 5-5 in FIG. 3.

DETAILED DESCRIPTION

Figure 1:
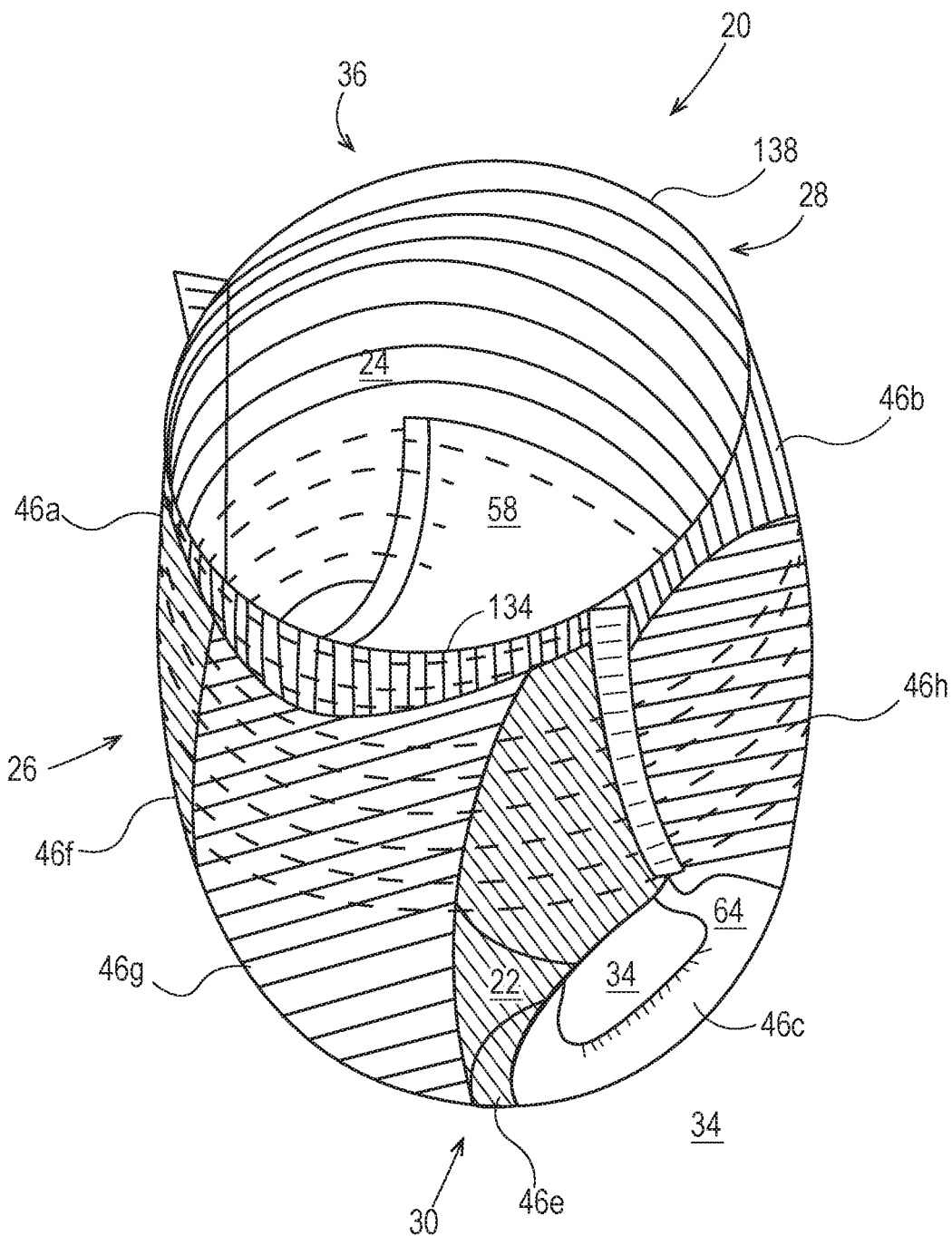
FIG. 1 is a perspective view of an exemplary disposable pull-on garment in a typical in-use configuration.

As used herein, the term "array" means a display of packages comprising disposable articles of different sizes having like article constructions (e.g., same elastomeric materials [compositionally and/or structurally] in the flaps, graphic elements) said packages having the same brand and/or sub-brand, and said packages oriented in proximity to each other in a given area of a retail store. An array is marketed as a line-up of products normally having like packaging elements (e.g., packaging material type, film, paper, dominant color, design theme, etc.) that convey to consumers that the different individual packages are part of a larger line-up. Arrays often have the same brand, for example, "Depend," and same sub-brand, for example, "for Women Underwear." A different array may have the brand "Depend" and the sub-brand "Silhouette For Women." The differences between the "for Women Underwear" array and the "Silhouette For Women" arrays include different elastomeric materials in the side flaps, where "for Women Underwear" comprises strands as the elastomeric material and "Silhouette For Women" comprises a film elastomeric material. Furthermore, the packaging is distinctly different in that "for Women Underwear" is packaged in a predominately green, film bag and "Silhouette For Women" is packaged in a predominately maroon box.

Further regarding "arrays," as another example of two separate "arrays" having the same brand, "Certainty," one line-up has the sub-brand "Women's Underwear." A different array may have the same brand "Certainty" and the sub-brand "Smooth Shape Briefs for Women." The differences between the "Women's Underwear" array and the "Smooth Shape Briefs for Women" arrays include different elastomeric materials in the side flaps, where "Women's Underwear" comprises strands as the elastomeric material and "Smooth Shape Briefs for Women" comprises a film elastomeric material. Furthermore, the packaging is distinctly different in that "Women's Underwear" is packaged in a predominately blue, film bag and "Smooth Shape Briefs for Women" is packaged in a predominately maroon box.

Arrays also often have the same trademarks, including trademarks of the brand, sub-brand, and/or features and/or benefits across the line-up.

As used herein, the term "on-line array" means an "array" distributed by a common on-line source.

As used herein, the term "pull-on garment" refers to articles of wear which have a defined waist opening and a pair of leg openings and which are pulled onto the body of the wearer by inserting the legs into the leg openings and pulling the article up over the waist. The term "disposable" is used herein to describe garments which are not intended to be laundered or otherwise restored or reused as a garment (i.e., they are intended to be discarded after a single use and to be recycled, composted or otherwise disposed of in an environmentally compatible manner). The pull-on garment may be "absorbent" such that it absorbs and contains the various exudates discharged from the body.

As used herein, the term "absorbent article" refers to pull-on garments worn by incontinent individuals, including adults, to absorb and contain urine, feces and/or menses. It should be understood, however, that the term absorbent article is also applicable to other garments such as incontinent briefs, feminine hygiene garments or panties, and the like.

As used herein, the term "belt" refers to waistband, ears, side-panels, back panels, etc. For instance, while the present disclosure illustrates articles comprising belt-style articles, the articles may alternatively comprise flaps as disclosed in U.S. Ser. No. 61/990,327, titled LENGTH-TO-HIP SILHOUETTES OF ADULT DISPOSABLE ABSORBENT ARTICLES AND ARRAYS, to Seitz, et al.

As used herein, the terms "elastic," "elastomer," and "elastomeric" refer to a material which generally is able to extend to a strain of at least 50% without breaking or rupturing, and is able to recover substantially to its original dimensions, accounting for set, after the deforming force has been removed.

As used herein, the term "joined" encompasses configurations whereby an element is directly secured to another element by affixing the element directly to the other element, and configurations whereby an element is indirectly secured to another element by affixing the element to intermediate member(s) which in turn are affixed to the other element.

As used herein, the term "visual characteristic" is intended to mean a visible, distinguishing or recognizable feature or attribute of a visible aspect of one or more elements of an absorbent article and/or an article of clothing, and/or a line of clothing. Non-limiting examples of visual characteristics are color, texture, pattern, form, and the like.

As used herein, the term "visible" is intended to mean attribute of feature which is visually perceived by an individual user or consumer. Generally for a consumer or user, the attribute should be visible in the range of about 0.25 feet (0.075 meters) to about 3 feet (0.91 meters). For a non-consumer or non-user, generally for an attribute to be visible, the distance will typically be greater than about 3 feet (0.91 meters). As used herein, "perceived" or "perception" is the ability to recognize an attribute or feature when the visual angle that the attribute or feature subtends is greater than about 5 minutes of visual arc and less than about 45 minutes of visual arc as determined by the following equation: Minutes of visual arc=3438*(length of the object/distance from object); wherein the length of the object=size of the object measured perpendicular to the line of sight, the distance from object=distance from the front of the eye to the object along the line of sight, and a minute of visual arc is $\frac{1}{60}^{th}$ of 1 degree.

As used herein, the term "color" is intended to mean an individual's perception of the spectral composition of visible light coming from a portion of an object. Color characteristics include hue, saturation and luminosity. Each is a separate color characteristic. Hue is the attribute of a color which allows it to be classified as a given color. Saturation, which is sometimes referred to as vividness, is the intensity of the color. Saturation is the degree of freedom from gray. Luminosity, sometimes referred to as value, is the degree of lightness (paleness) or darkness in a color. For example, a blue with white added is a pale color, e.g. baby blue and blue with black added is a dark color, e.g. navy blue. A measurement of hue, saturation and luminosity are described in more detail below.

As used herein, the term "form" is used to describe an individual's perception of the spatial variation of visible light due to the bulk shape and structure of a portion of an object in three dimensions. Stated another way, form is shape and structure of an item which distinguishes it from its surrounding which causes a spatially discontinuous change in light that is transmitted through or reflected from an item.

As used herein, the term "texture" is used to describe the individual's perception of the spatial variation of visible light due to surface structure of a portion of an object in two dimensions. Textures can be visual effects generated by surface roughness and visual illusion created by mere color or pattern. Texture may be the result of the natural characteristics of a given material as a result of the material formation process. Textures may also be imparted to a material using techniques known to those skilled in the art including, for example, printing, embossing, bonding, aperturing and the like.

As used herein, the term "pattern" is used to describe the individual's perception of spatial variation of visible light due to contrasts in spatial variation of light due to the color, form, and texture of a portion of an object incorporated into the object by the manufactory of the elements. This contrast creates various visual distinct regions or lines sometimes referred to as "figures" within its surrounding sometimes referred to as "ground." Patterns can be formed by combinations of contrasting color, form, and texture relative to its surroundings. An element can have more than one pattern, but each pattern would be distinguishable, recognizable, and separate from the other patterns on the element. Pattern is also a term used to describe the observer's perception of combined effect of more than one color, form, or texture within a portion of an observer's field of view. Patterns may have a "length," "extent," "shape," "position" and "orientation." Each is a pattern characteristic within the scope of the present invention. Length is the perceived distance along the major axis of the pattern. The "major axis" is the axis of the longest symmetry. The extent of the pattern is the area of the pattern. Shape is simply the shape of the pattern. Position is the location of the pattern relative to its surroundings. And orientation is position of the major axis of the pattern relative to its surroundings.

As used herein, the term "match" or "matched" is used to describe the way or degree two items visually fit together. For example, two items are considered matched if some aspects of one of the items are identical to similar aspects of another item. In one form of match, two items resemble each other are said to match.

As used herein, the term "coordinate" or "coordination" is used to describe how two components or elements of the absorbent article and the article of clothing, and/or line of clothing visually belong together. Visual characteristics are said to coordinate if one aspect of the visual characteristic is the same or falls within limits described with this specification. Visual characteristics are also said to coordinate if they match. Components or elements are considered to be coordinated if they match. Graphics are considered to be coordinated if they match. An absorbent article and an article of clothing are considered to be coordinated if they match. An absorbent article and a line of clothing are considered to be coordinated if they match. Colors may be coordinated if they have a hue, luminosity or saturation that match within limits described below.

Please note that throughout the specification, structural elements of the present disclosure may be referred to generally, like side edges 47, which is meant to encompass side edge 47a and side edge 47b.

Figure 2:
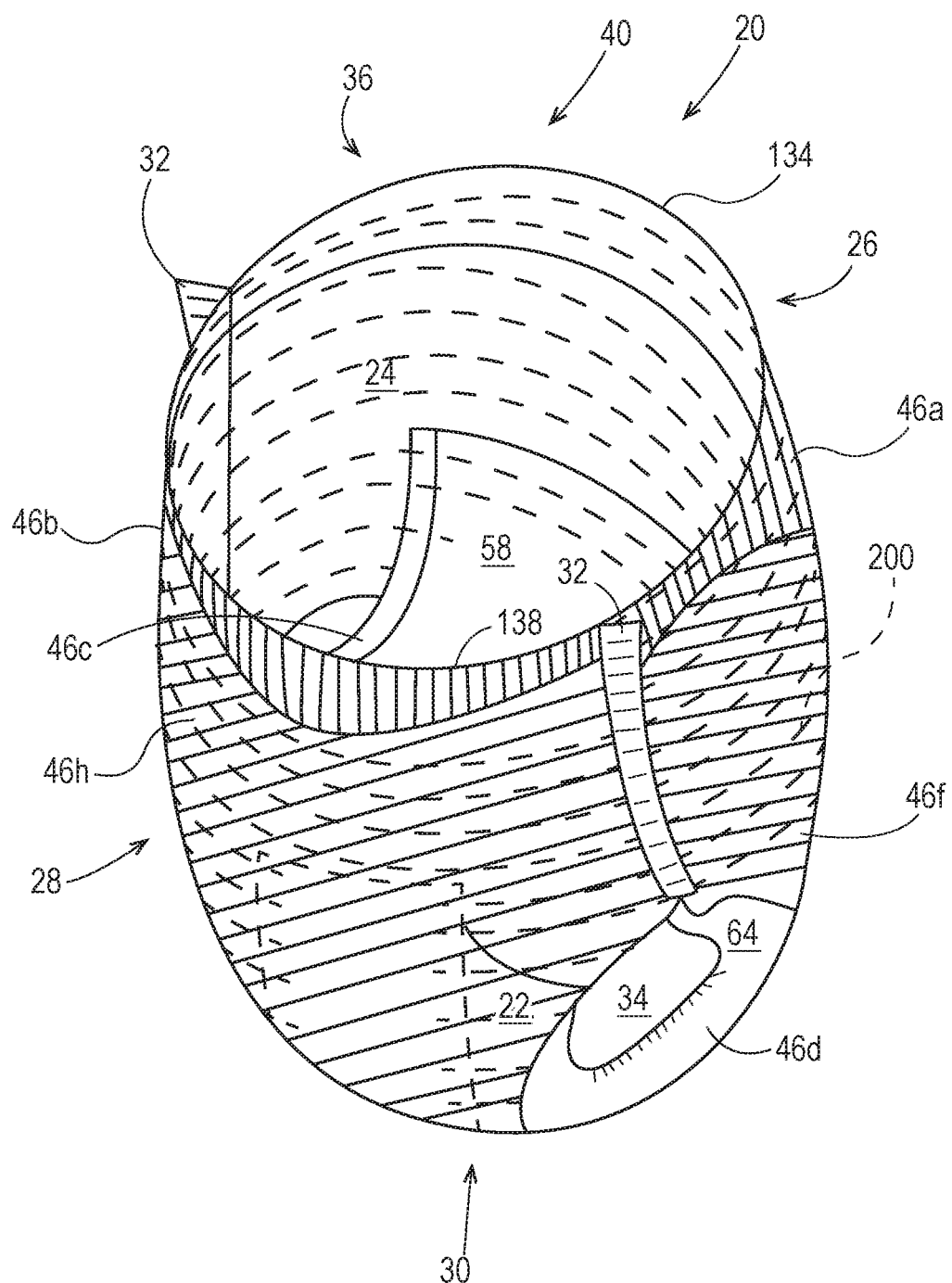
FIG. 2 is a perspective view of the exemplary disposable pull-on garment of FIG. 1.
Figure 6:
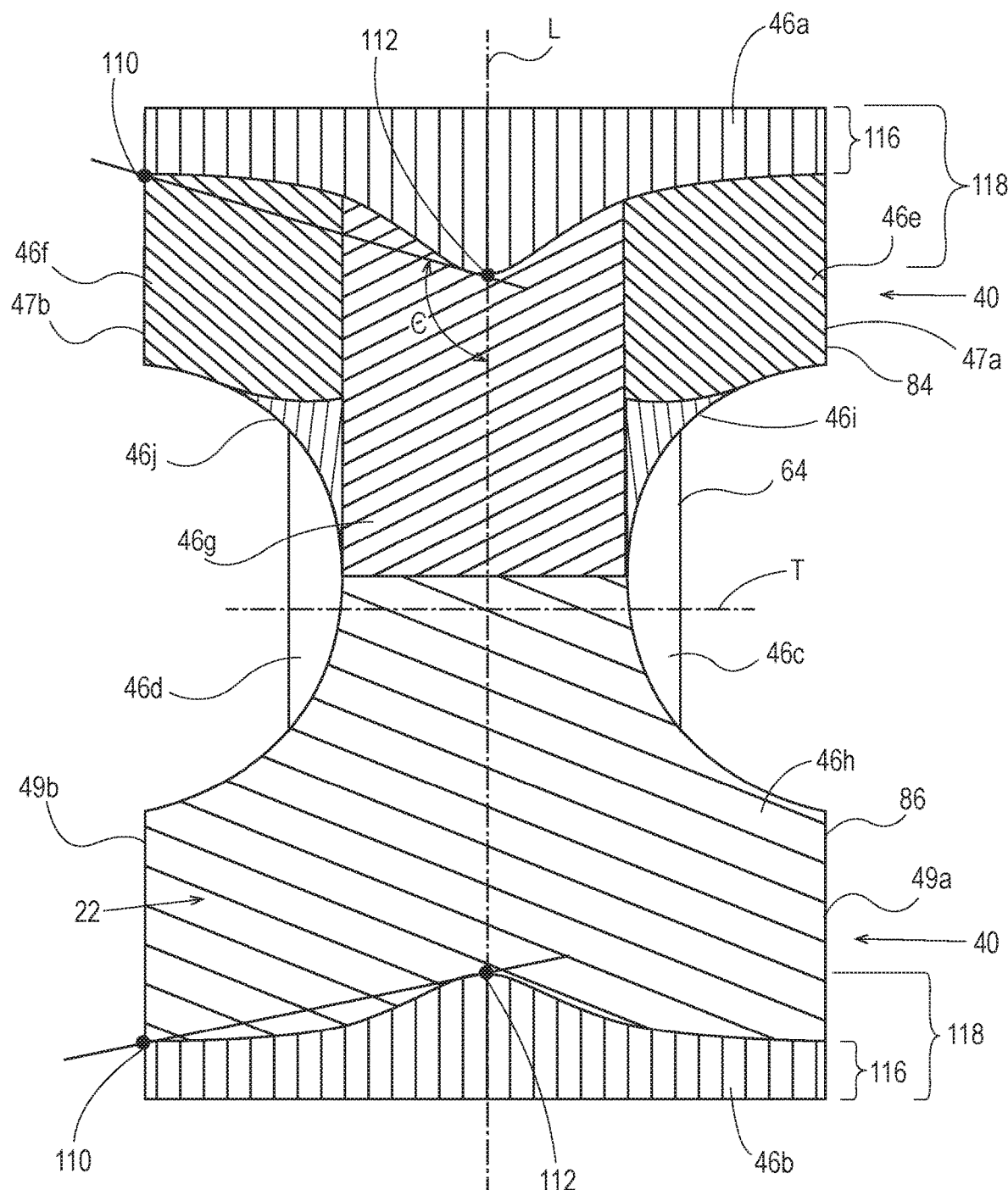
FIGS. 6 and 7 are plan views of embodiments of a pull-on garment in its flat uncontracted condition showing their exterior surfaces.
Figure 7:
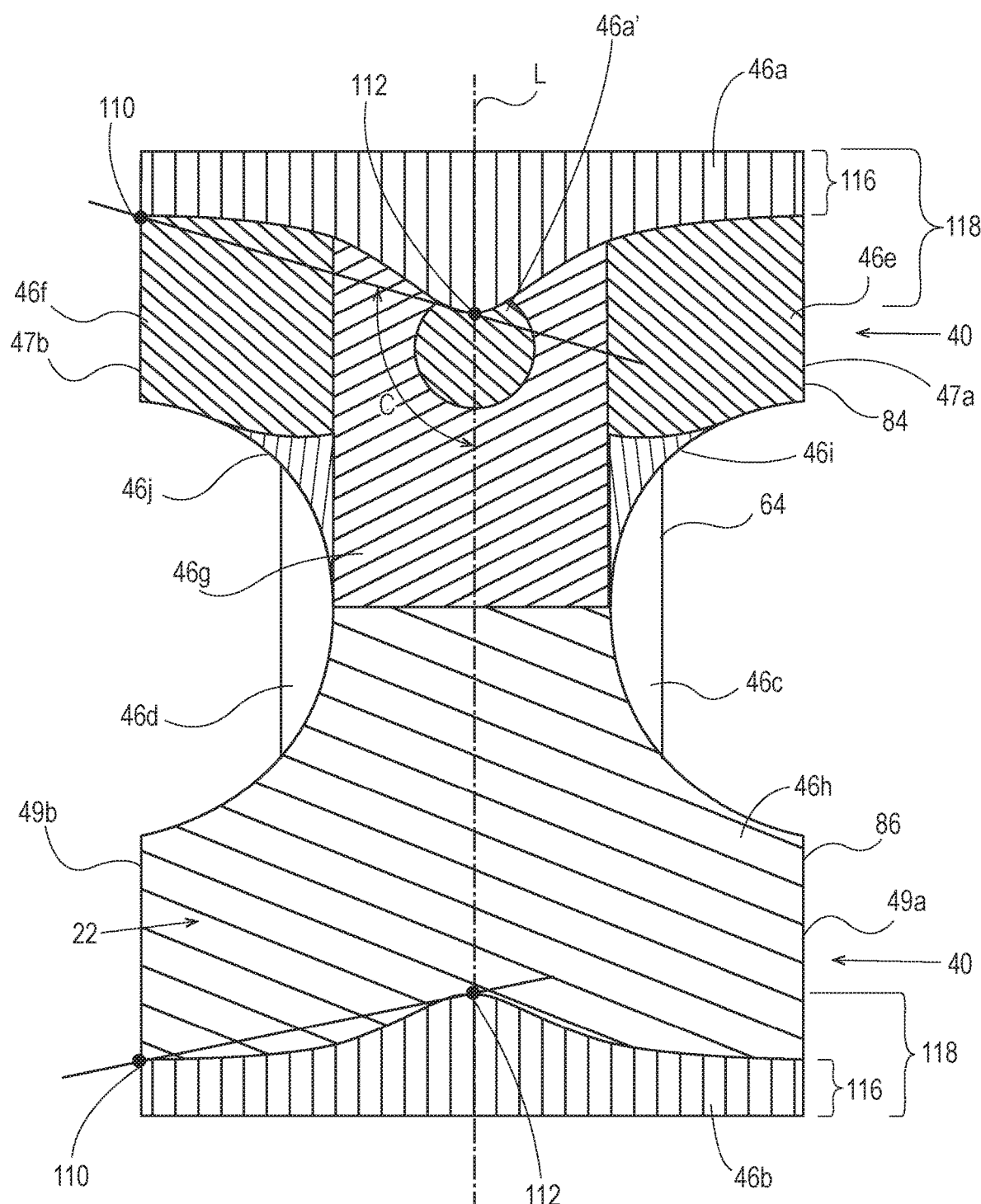

FIGS. 1 and 2 are perspective views of the absorbent article 20. As shown in FIGS. 6 and 7, the absorbent article 20 has a longitudinal centerline L and a transverse centerline T. The absorbent article 20 has an outer (or "exterior") surface 22, an inner surface 24 opposed to the outer surface 22, a front region 26 (or "front waist region"), a back region 28 ("or back waist region"), a crotch region 30, and seams 32 which join the front region 26 and the back region 28 to form two leg openings 34 and a waist opening 36.

Figure 3:
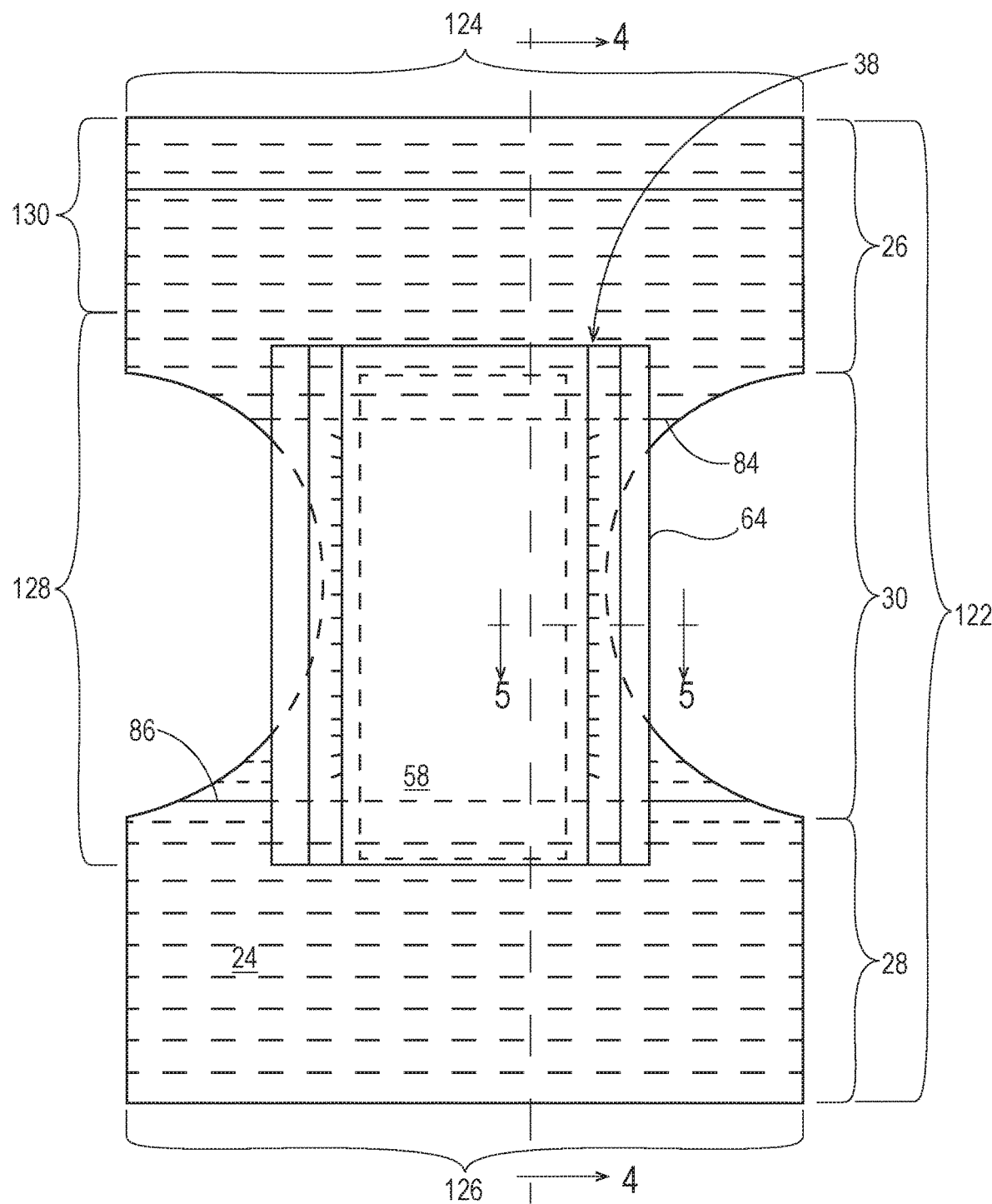
FIG. 3 is a plan view of the pull-on garment in its flat uncontracted condition showing the inner surface.
Figure 4B:
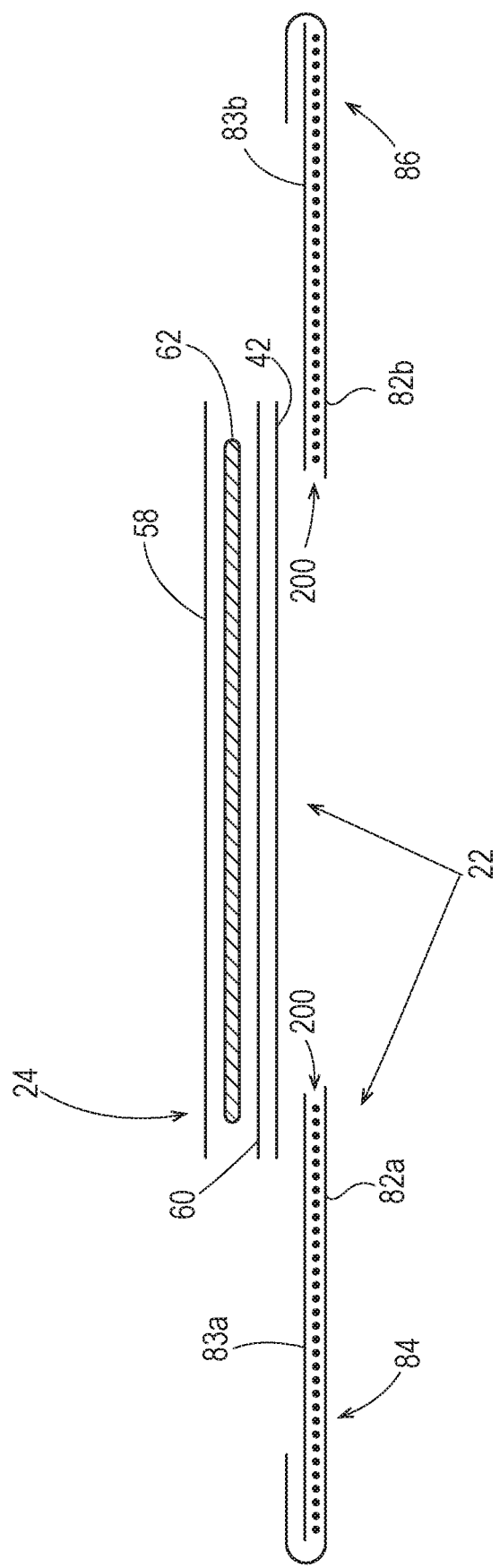
Figure 4C:
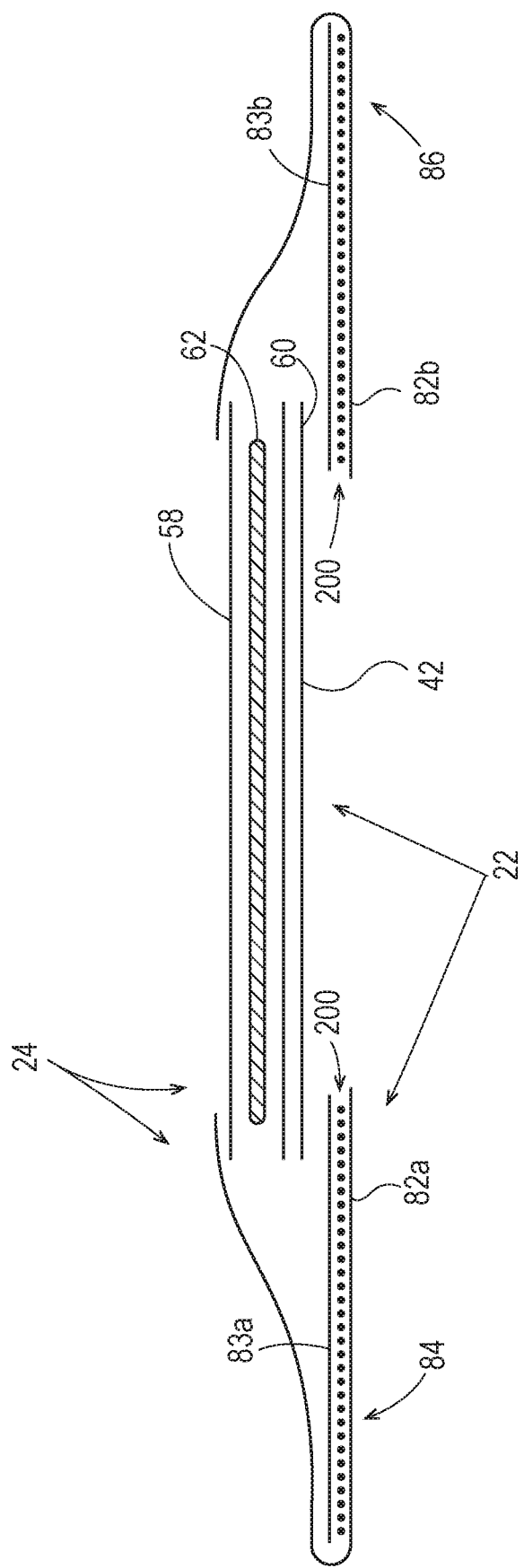

In the embodiment shown in FIGS. 1 and 3, the absorbent article 20 comprises an absorbent main body 38 (hereinafter may be referred to as "main body" or "center chassis") to cover the crotch area of the wearer and a belt 40 extending transversely about the waist opening 36. As shown in FIGS. 4A-C, the absorbent article 20 may also comprise an outer cover layer 42 to cover the main body 38. The belt 40 defines the waist opening 36. The belt 40, the main body 38 and/or the outer cover layer 42, and/or the cuffs 64 may jointly define the leg opening 34.

In the embodiment shown in FIG. 2 the absorbent article 20 comprises an absorbent main body 38 to cover the crotch area of the wearer and a belt 40 extending transversely about the waist opening 36. The absorbent article 20 may also comprise an outer cover layer 42 to cover the main body 38. The belt 40 defines the waist opening 36. In this embodiment, the belt 40, the main body 38 and/or the outer cover layer 42 jointly define the leg opening 34. One or more of the belt layers may extend from a first waist edge 134 in a first waist region 26 through the crotch region 30 to a longitudinally opposing second waist edge 138 in a second waist region 28 and may form a portion or the whole of the outer surface of the absorbent article 20.

The absorbent main body 38 absorbs and contains body exudates. In the embodiment shown in FIGS. 6 and 7, the main body 38 has a generally rectangular shape having a longitudinal centerline L, a transverse centerline T, left and right longitudinally extending side edges 48a and b (hereinafter may be referred to as "longitudinal side edge(s)") and front and back transversely extending end edges 50a and 50 (hereinafter may be referred to as "transverse end edge(s)").

In the embodiments shown in FIGS. 4A-C, the absorbent articles 20 may comprises front and rear (or "back") extensible belts 84, 86 disposed in the front and rear (or "back") waist regions 26, 28 respectively (and in some embodiments may extend into the crotch region 30) and intended to encircle at least a portion of the waist of the wearer, the front and rear belts 84, 86 being connected by the main body 38. The front and rear belts 84 and 86 may be formed from a first outer belt layer 82 (that may also serve as the outer cover layer 42 of the main body 38) and may extend from a first waist edge 134 in a first waist region 26 through the crotch region 30 to a longitudinally opposed second waist edge 138 in a second waist region 28 and forming a portion or the entire outer surface 22 of the absorbent article 20. Alternatively, the outer belt layer 82 may have a front portion 82a longitudinally separated from a back portion 82b. The outer belt layer may wrap the front waist edge 134 and the rear waist edge 138 and overlap second inner belt layers 83a and 83b or may overlap a portion of the main body 38 (including the topsheet 58, as shown in FIG. 4C). The inner belt layer 83 may also be continuous from the front waist edge 134 to the rear waist edge 138.

The second belt layer 83a and b (e.g., an "inner belt web(s)") may form a portion of the inner surface 24 of the absorbent article 20. The second belt layer 83 may be formed of two longitudinally spaced webs of material. The first and second belt portions may also comprise an elastomeric material 200 (e.g., "elastic elements" or "elastics") disposed between the first and second belt layers. The elastomeric material may comprise elastic strands, elastomeric films, elastomeric ribbons, elastomeric nonwovens, elastomeric filaments, elastomeric adhesives, elastomeric foams, scrims, apertured films (as described in U.S. Pat. Nos. 6,410,129; 7,087,287; and U.S. Pub. No. 2007-0287348), or combinations thereof. A portion of the elastomeric material 200 may be directly combined with the outer cover layer. The main body 38 ("central or center chassis") of the absorbent article may comprise a backsheet 60, a topsheet 58, and an absorbent core 62 disposed between the topsheet 58 and the backsheet 60. The main body 38, as well as the first belt layer 82, may form a portion of the outer surface 22 as shown in FIG. 4C. The main body, as well as the first and second belt layers 82 and 83, may form a portion of the inner surface 24. In addition, the main body 38 may comprise elasticized cuffs 64 disposed at or adjacent to (or may form) the side edges 48 of the main body 38.

The first and second belt layers 82, 83 may be formed of substantially the same material or may comprise different materials. Likewise, the front and rear belts 84, 86 may be formed of substantially the same material or may comprise different materials. The first and second belt layers 82 and 83 may be formed from nonwovens, films, apertured films (as described in U.S. Pat. Nos. 6,410,129; 7,087,287; and U.S. Pub. No. 2007-0287348), foams, woven materials or combinations thereof.

Additional lateral extensibility in the main body 38 and/or the front and rear belts 84,86 (making up the belt 40) may be provided in a variety of ways. For example, a material or materials from which the main body 38 and/or the belt 40 is made may be pleated by any of many known methods. Alternatively, all or a portion of the main body 38 may be made of a formed web material or a formed laminate of web materials like those described in U.S. Pat. No. 5,518,801 issued on 21 May 1996 in the name of Chappell et al. This formed web material includes distinct laterally extending regions in which the original material has been altered by embossing or another method of deformation to create a pattern of generally longitudinally oriented alternating ridges and valleys and also includes laterally extending unaltered regions between the laterally extending altered regions. The formed web material can be extended in a direction perpendicular to the ridges up to the point where the ridges and valleys flatten with substantially less force than is required to extend beyond that point. In addition to lateral extensibility, the creation of a formed laminate web as described above provides a main body 38, backsheet 60 and or the outer cover nonwovens 42, 82 with improved texture and cloth-like appearance and feel. The deformation creates a cloth-like pattern in the film and/or the nonwovens and increases the loft of the nonwoven in multi-layer film and nonwoven laminate backsheets.

Alternatively, a portion of the absorbent article can be ring-rolled and thus rendered highly extensible as described in U.S. Pat. No. 5,366,782 (issued Nov. 22, 1994 to Curro, et al). Specifically, a ring-rolling apparatus includes opposing rolls having intermeshing teeth that incrementally stretch and thereby plastically deform the material forming the absorbent article (or a portion thereof) thereby rendering the article extensible in the ring-rolled regions. In one embodiment, portions of the absorbent article 20 can be ring-rolled in a portion of at least one of the front or rear waist regions, for example the portion of the main body 38 underlying and/or immediately adjacent one or both of the front and rear belts 84, 86, while other regions may comprise a structured elastic-like formed web material. The article may be ring-rolled across the entire width in one or both of the waist regions or alternatively may be ring-rolled over only a portion of the main body 38 width or over only a portion of one or both of the belts 84, 86.

Topsheet

In one embodiment, the absorbent article 20 may comprise a topsheet 58. The topsheet 58 may be compliant, soft feeling, and non-irritating to the wearer's skin and may be elastically stretchable in one or more directions. Further, the topsheet 58 may be liquid pervious, permitting liquids (e.g., menses, urine, and/or runny feces) to penetrate through its thickness. Various topsheets may also comprise a hydrophilic material, for example, which is configured to draw bodily fluids into an absorbent core 62 when these fluids are expelled from the body. A suitable topsheet 58 may be manufactured from a wide range of materials, such as woven and nonwoven materials, apertured or hydroformed thermoplastic films, apertured nonwovens, porous foams, reticulated foams, reticulated thermoplastic films, and/or thermoplastic scrims, for example. Suitable apertured films may comprise those described in U.S. Pat. Nos. 3,929,135, 4,324,246, 4,342,314, 4,463,045, 5,006,394, 5,628,097, 5,916,661, 6,545,197, and 6,107,539.

Apertured film or nonwoven topsheets typically may be pervious to bodily exudates, yet non-absorbent, and have a reduced tendency to allow fluids to pass back through and rewet the wearer's skin. Suitable woven and nonwoven materials may comprise natural fibers, such as, for example, wood or cotton fibers, synthetic fibers, such as, for example, polyester, polypropylene, or polyethylene fibers, or combinations thereof. If the topsheet 58 comprises fibers, the fibers may be spunbond, carded, wet-laid, meltblown, hydroentangled, or otherwise processed, for example, as is generally known in the art.

The topsheet 58 may comprise a skin care lotion. Examples of suitable lotions include, but are not limited to, those described in U.S. Pat. Nos. 5,607,760; 5,609,587; 5,635,191; 5,643,588; and 5,968,025, and as described in U.S. Application No. 61/391,353, and as described in U.S. Pub. No. 2014-0257216. Beyond these compositions, the absorbent article may comprise soluble cyclodextrin derivatives such as those described in U.S. Pub. No. 2014/0274870.

Additionally, the topsheet of the present disclosure may be a tufted laminate web as disclosed in U.S. Pat. No. 7,410,683, and/or may be an apertured web as disclosed in PCT/CN2014/083769 having an international filing date of Aug. 6, 2014.

Absorbent Core

In various embodiments, the absorbent article 20 may comprise an absorbent core (also referred to as an "absorbent member" or "absorbent assembly" or "absorbent structure" or "absorbent composite") 62 that is disposed between the topsheet 58 and the backsheet 60. In one embodiment, more than one absorbent core 62 or more than one absorbent core layer may be provided in an absorbent article 20, for example. Suitable absorbent cores that may be used are disclosed in U.S. Pat. Nos. 4,610,678; 4,673,402; 4,888,231; and 4,834,735.

In one embodiment, the absorbent core 62 may comprise cellulosic airfelt material. For instance, such absorbent cores may comprise less than about 40%, 30%, 20%, 10%, 5%, or even 1% of the cellulosic airfelt material as determined by weight. Additionally, such an absorbent core may be primarily comprised of an absorbent gelling material in amounts of at least about 60%, 70%, 80%, 85%, 90%, 95%, or even about 100% (i.e., airfelt free) as determined by weight. Furthermore, a portion of the absorbent core may comprise a microfiber glue (if applicable). Such absorbent cores, microfiber glues, and absorbent gelling materials are described in U.S. Pat. Nos. 5,599,335; 5,562,646; 5,669,894; 6,790,798; and 7,521,587 and in U.S. Pat. Publ. No. 2004/0158212.

In one embodiment, the core, including multiple layers making up a core system, may be printed and embossed as described in U.S. Pat. No. 8,536,401.

In one embodiment, the core may be separable from the chassis as disclosed in U.S. Pat. Nos. 6,989,006; 7,381,202; 7,175,613; 7,824,386; 7,766,887; and 6,989,005.

In one embodiment, the absorbent article 20 of the present disclosure, and particularly, a portion where the absorbent member is disposed, may have a body fluid absorption rate greater than 3 g/sec according to U.S. Pat. No. 6,649,810. According to U.S. Pat. No. 6,649,810, the expression "the portion (of the absorbent article) where the absorbent member is disposed" is intended to mean the portion occupied by the absorbent member when the absorbent article is flatly unfolded and seen in its plan view.

In one embodiment, the absorbent structure may have an intake factor greater than 3 according to U.S. Pat. No. 7,073,373, wherein the intake factor is defined as the absorbent core permeability divided by the normalized retention capacity (which is defined by the Retention Capacity Test—also according to U.S. Pat. No. 7,073,373).

In one embodiment, the absorbent composite has a body fluid absorption greater than 75 g/100 $cm^2$, according to U.S. Pat. No. 6,649,810.

In one embodiment, a target location of the absorbent article may have a wicking value greater than 36%, according to U.S. Pat. No. 6,383,960.

In one embodiment, the absorbent article may have a bending stiffness between 0.05-1.0 gf, according to U.S. Pat. No. 5,810,796.

In one embodiment, the absorbent article may have a crotch fluid absorption rate greater than 3 g/sec according to U.S. Pat. No. 6,649,810. In one embodiment, a freeze-dried composite of the absorbent composite may have an intake rate of at least about 1.9 cubic centimeters (cc) of liquid/second at 80% composite saturation according to U.S. Pat. No. 6,689,934.

In one embodiment, the absorbent core 62 may comprise channels as described in U.S. Pat. No. 8,568,566; U.S. Pub. Nos. 2012-316046, 2014-027066, 2014-163500, 2014-163506, 2014-163511, 2012-316526, 2012-316527, 2012-316528, 2012-316529, 2012-316523, 2014-163501, 2014-163502, 2014-163503; and European Pub. Nos. 2532328, 2532329, 2717823, 2717820, 2717821, 2717822, 2532332, 2740449, and 2740452.

Backsheet

The absorbent article 20 may comprise a backsheet 60. The backsheet 60 may be impervious, or at least partially impervious, to fluids or body exudates (e.g., menses, urine, and/or runny feces) and may be manufactured from a thin plastic film, although other flexible liquid impervious materials may also be used. The backsheet 60 may prevent the bodily exudates or fluids absorbed and contained in an absorbent core 62 of the absorbent article 20 from wetting articles of clothing that contact the absorbent article 20. The backsheet 60 may comprise a woven or nonwoven material, polymeric films such as thermoplastic films of polyethylene or polypropylene, and/or a multi-layer or composite materials comprising a film and a nonwoven material (e.g., having an inner film layer 60 and an outer nonwoven layer 42). A suitable backsheet may comprise a polyethylene film having a thickness of from about 0.012 mm (0.5 mils) to about 0.051 mm (2.0 mils). Examples of polyethylene films are manufactured by Clopay Corporation of Cincinnati, Ohio, under the designation BR-120 and BR-121, and by Tredegar Film Products of Terre Haute, Ind., under the designation XP-39385.

One suitable material for the backsheet 60 can be a liquid impervious thermoplastic film having a thickness of from about 0.012 mm (0.50 mil) to about 0.051 mm (2.0 mils), for example including polyethylene or polypropylene. Typically, the backsheet 60 can have a basis weight of from about 5 $g/m^2$ to about 35 $g/m^2$. The backsheet 60 can be typically positioned adjacent the outer-facing surface of the absorbent core and can be joined thereto. For example, the backsheet 60 may be secured to the absorbent core 62 by a uniform continuous layer of adhesive, a patterned layer of adhesive, or an array of separate lines, spirals, or spots of adhesive. Illustrative, but non-limiting adhesives, include adhesives manufactured by H. B. Fuller Company of St. Paul, Minn., U.S.A., and marketed as HL-1358J. An example of a suitable attachment device including an open pattern network of filaments of adhesive is disclosed in U.S. Pat. No. 4,573,986. Another suitable attachment device including several lines of adhesive filaments swirled into a spiral pattern is illustrated by the apparatus and methods shown in U.S. Pat. Nos. 3,911,173; 4,785,996; and 4,842,666. Alternatively, the attachment device may include heat bonds, pressure bonds, ultrasonic bonds, dynamic mechanical bonds, or any other suitable attachment device or combinations of these attachment devices.

In one embodiment, the backsheet 60 may be embossed and/or matte-finished to provide a more cloth-like appearance. Further, the backsheet 60 may permit vapors to escape from the absorbent core 62 of the absorbent article 20 (such that the backsheet 60 is breathable) while still preventing, or at least inhibiting, fluids or body exudates from passing through the backsheet 60.

Leg Cuffs

The cuff 64 (inner cuff 64a and outer cuff 64b) provides improved containment of liquids and other body exudates. A suitable embodiment of the cuff 64 shown in FIGS. 5A-C comprises a single layer of material which may be folded to form a barrier leg cuff having two layers. The cuff 64 extends from the side of the main body at or adjacent, or forming part of, the longitudinal side edge 48 toward the longitudinal centerline L.

Figure 5A:
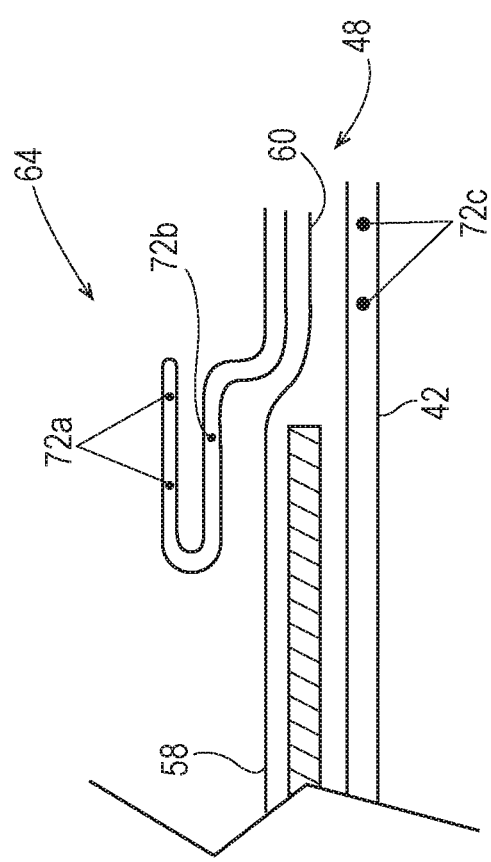

The cuff 64 may have first, second, and third barrier cuff elastic materials 72a, b, and c; each of the elastic materials may be the same or different. A distal portion of the cuff 64 may be adhered to a distal portion of the backsheet film 60, and another portion of the cuff 64 may be adhered to the topsheet via adhesive 118 as illustrated in FIGS. 5A-C. Beyond these cuff 64 configurations, other suitable examples of cuffs 64 that may be used herein are disclosed in U.S. Ser. No. 13/457,521, filed Apr. 27, 2012, including the configurations disclosed by FIGS. 8a-t. For instance, as illustrated in FIG. 5B, the cuff may be two-piece. And, the cuff 64 may be joined to the backsheet with a no leak bead 118' that runs along the entire longitudinal length of the cuff 64 and/or the backsheet film 60.

As shown in FIG. 5A, the backsheet film 60, the outer-cover nonwoven 42, and both layers of the cuff 64 may co-terminate at the side edge 48. Alternatively, as shown in FIGS. 5B and C, the distal end of the cuff 64 may extend beyond the other materials to form at least a portion of the side edge 48 in a manner that exposes at least a portion of the cuff when the article 20 is worn, such that a more finished folded leg edge is achieved.

Other suitable cuffs 64 may be configured as those described in U.S. Pat. Nos. 3,860,003, 4,909,803, 4,695,278, 4,795,454, 4,704,115, and 4,909,803, and U.S. Pat. Publ. No. 2009/0312730.

Visual Characteristics

Of the visual characteristics, color is a characteristic that is simple to quantify. Colors have some basic characteristics, including hue, saturation, and luminosity. Each of these terms is described above. A given color may be varied by changing the saturation and luminosity. Saturation is changed by adding a neutral color, black, white, or gray. Luminosity may be changed by adding a brightener to a given color. In the present invention, if two colors have the same hue, whether or not they are different in saturation or luminosity, the two colors are considered coordinated. Likewise, if two colors have the same saturation or the same luminosity, the colors are considered to be coordinated. Colors which have the same hue, saturation and luminosity are considered matched. Color may be imparted by any means know to those skilled in the art, including, for example, printing, dyeing, pigmenting and the like.

In an embodiment, white is generally not considered as a color is used as the coordinating feature if white is a predominate color on the element being coordinated. This is because white is the predominate color of absorbent articles, and thus white does not lend itself as a coordinating color. However, white may be a coordinating color, provided that it is not used as the predominate color on the components or surfaces being coordinated. Stated another way, white may be a coordinating color if it is used as an accent or a non-dominate color. By "non-dominate color" it is intended mean a color which encompasses less than 50%, desirable less than 30%, of the surface area of a surface.

In an embodiment, the first and second visual characteristics may be configured as first and second colors. Each of the first and second colors may be different from one another by having a different hue. One or more colors may also be different by virtue of having a different luminosity and/or saturation/vividness. Saturation/vividness is the intensity of the color from pale to dark. Colors of different hues can be coordinated or match by virtue of having the same luminosity or saturation. For example, pale or pastel colors of different hues tend to blend together or appear that they belong together or are matched due to the fact that the saturation levels are similar. Other factors in color differences include different finishes e.g. gloss/finish verses a matte finish. Matte finishes tend to diffuse or scatter light compared to a gloss finish, which is specular.

Printing may generally be characterized as an industrial process in which an image is reproduced on a substrate, such as paper, polyolefin film, or nonwoven fabric. There are various classes of printing processes, which may include stencil and screen printing, relief printing, planographic printing, intaglio printing, and electronic printing. Stencil and screen printing may be used for printing T-shirts, signage, banners, billboards, and the like. Examples of relief printing may include letterpress and flexography. Examples of planographic printing may include offset lithography, screenless lithography, collotype, and waterless printing. In addition, examples of intaglio printing may include gravure, steel-die, and copper-plate engraving. Examples of electronic printing may include electrostatic, magnetographic, ion or electron deposition, and ink-jet printing. It is it to be appreciated that various types of printing processes may be used to create the graphics (e.g., disclosed herein. For example, in some embodiments, it may be preferable to use flexography. In particular, flexography may utilize printing plates made of rubber or plastic with a slightly raised image thereon. The inked plates are rotated on a cylinder which transfers the image to the substrate. Flexography may be a relatively high-speed print process that uses fast-drying inks. In addition, flexography can be used to print continuous patterns on many types of absorbent and non-absorbent materials. Other embodiments may utilize gravure printing. More particularly, gravure printing utilizes an image etched on the surface of a metal plate. The etched area is filled with ink and the plate is rotated on a cylinder that transfers the image to the substrate. Still other embodiments may utilize ink-jet printing. Ink-jet is a non-impact dot-matrix printing technology in which droplets of ink are jetted from a small aperture directly to a specified position on a media to create an image. Two examples of inkjet technologies include thermal bubble or bubble jet and piezoelectric. Thermal bubble uses heat to apply to the ink, while piezoelectric uses a crystal and an electric charge to apply the ink.

In addition to the aforementioned various types of printing processes, it is to be appreciated that various types of inks or ink systems may be applied to various types of substrates to create the disclosed patterns, such as solvent-based, water-based, and UV-cured inks. The primary difference among the ink systems is the method used for drying or curing the ink. For example, solvent-based and water-based inks are dried by evaporation, while UV-cured inks are cured by chemical reactions. Inks may also include components, such as solvents, colorants, resins, additives, and (for ultraviolet inks only) UV-curing compounds, that are responsible for various functions.

Two colors are considered coordinated if they have first and second hues that are the same. Colors of different hues are also considered coordinated if they have a value (luminosity) difference of less than 5% of maximum, alternatively less than 3% of maximum or alternatively less than 1% of maximum. Colors of different hues are also considered coordinated if they have a saturation difference of less than 5% of maximum, alternatively less than 3% of maximum or alternatively less than 2.5% of maximum.

In an embodiment, color matching of visible surfaces is determined by the color of an absorbent article and the corresponding color of the clothing and/or line of clothing having a specified CIELab color space hue difference ($\Delta H$). Characterizing color matching by the hue difference is desirable in that hue difference accounts for and considers all three dimensions within CIELab. While not being limited to this theory, such a three-dimensional measurement is believed to more fully characterize the difference in two colors.

Figure 8:
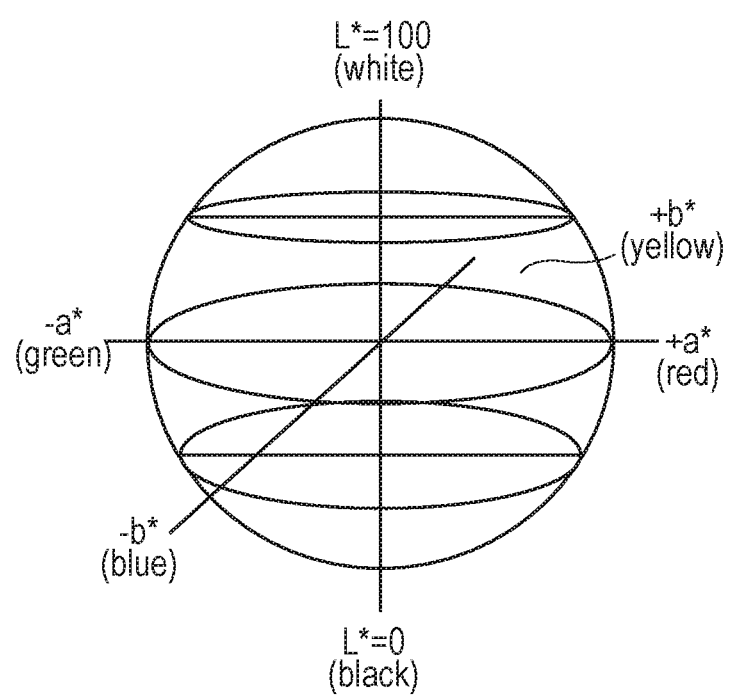
FIG. 8 is an illustration of three axes (respectively for the L*, a*, and b* value of a given color) used with the CIELAB color scale.

CIELAB is a conventional color model used to describe colors visible to the human eye. FIG. 8 is an illustration of three axes (respectively for the L*, a*, and b* value of a given color) used with the CIELAB color scale. When a color is defined according to the CIELAB color scale, L* represents lightness (0=black, 100=white), a* and b* independently each represent a two color axis, a* representing a red/green axis (+a=red, −a=green), while b* represents a yellow/blue axis (+b=yellow, −b=blue). The maximum for L* is 100, which represents a perfect reflecting diffuser, and the minimum for L* is zero, which represents black. The a* and b* axes have no specific numerical limits. The CIELAB color scale is an approximate uniform color scale, wherein the differences between points plotted in the color space correspond to visual differences between the colors plotted. Based on the L*, a*, and b* values for a first color (i.e. $L_1$, $a_1$, $b_1$) and a second color (i.e. $L_2$, $a_2$, $b_2$), the difference between the colors (i.e. $\Delta E$) can be calculated using the following formula:

$$\Delta E = \sqrt{(\Delta L^{*2} + \Delta a^{*2} + \Delta b^{*2})}$$

wherein, $\Delta L^* = L_1 - L_2$;
$\Delta a^* = a_1 - a_2$; and
$\Delta b^* = b_1 - b_2$.

The L*a*b* values for each zone of color in the graphic may be determined in various ways. For example, the L*a*b* values of the color zones may be determined by using ink with relatively known L*a*b* values. Alternatively, the L*a*b* values in a zone can be determined from the electronic file that is generated when a pattern is created. In such a case, the L*a*b* values may be obtained with a computer equipped with a software that can provide the L*a*b* value of a selected area. A non-limiting example of such software may be Adobe Photoshop®. In another embodiment, the L*a*b* values of various color zones on a graphic can be measured directly from the printed substrate that bears the design inspiring the graphic. A suitable procedure for measuring the L*a*b* values of a color zone is provided below.

In an embodiment, color measurements are performed using a commercial flat bed scanner capable of 4800 dpi, at 16 bit color depth, such as an Epson Perfection V500 Photo scanner (Epson America, Long Beach, Calif.). Each scan is calibrated against Pantone standards, and measurements made using Adobe Photoshop CS3 Extended Edition (Adobe Systems, Inc, San Jose, Calif.). The sample is measured on the printed side of the substrate. For example, if a laminate consist of a nonwoven and a film where the printing is on the film and sandwiched between the film and nonwoven, the nonwoven is removed before the printing on the film is measured.

Scans are calibrated using the Pantone Process Colors standard from the Pantone Formula Guide—Uncoated Papers (Pantone, Carlstadt, N.J.). CIE L*a*b* values are measured for the Pantone standard for each color, i.e., Process Yellow U, Process Magenta U, Process Cyan U, Process Black U, and the White uncoated paper. Tristimulus colors are measured according to ASTM Method E1164-07 (Standard Practice for Obtaining Spectrophotometric Data for Object-Color Evaluation) using a Hunter Labscan XE (HunterLab, Reston, Va.) with HunterLab Universal Software vs. 40.10 with the following settings: Scale CIELAB, 0/45 StdMode, Area View 0.50 in., Port Size 0.70 in., UV filter Nominal. During measurement the standard is backed using the white calibration plate provided by HunterLab. To increase the reliability of the measurement, each color should be measured at least in triplicate and averaged. The sample is placed on the scanner with the printed-side toward the sensor. The Pantone standard is also placed on the scanner such that the sample and standard are both captured in the same image.

The scan is collected at 1200 dpi at 8 bit color depth into Photoshop for objects with a primary dimension of greater than 3 mm, and at 2400 dpi, 8 bit color depth for objects with a primary dimension of less than 3 mm. Within Photoshop, the image is transformed into a Lab, 8 bit image (note in this version of Photoshop, L*a*b* is imprecisely denoted as Lab). Using the "Levels" command, the L channel of the image is adjusted to read within 2 units for each of the yellow, magenta, cyan, black and white colors on the Pantone standard. L*a*b* values are measured using the Color Sampler Tool using an 11 by 11 average sample size.

The graphic may be selected to be printed on a suitable area for printing on any surface suitable for printing on the absorbent article. In an embodiment, the graphic is to be printed on the backsheet of an absorbent article. In another embodiment, it is to be printed on the ear of a diaper. In an embodiment, the substrate has a basis weight of less than or equal to 20 gsm.

In an embodiment, the substrate has a low modulus, i.e. ≤20 Newtons/cm. In another embodiment, the modulus of the substrate is from 16 to 20 N/cm. In another embodiment, the modulus is ≤16 N/cm. Applicants have learned that high winding speeds of 1000 feet per minute or more, along with various film properties, can impart defects into the wound layers of film during winding. For example, non-uniform tensions and/or pressures are oftentimes imparted to the film during winding (e.g., at the outermost wound layers and near the core of the roll) due to various factors such as tension variations in the winding device (e.g., tolerance run-outs in the winding cylinder), film stability at the winding device, caliper control of the film, etc. The resulting unevenness between the two wound layers (e.g., the outermost wound layer and an immediately underlying wound layer) can produce a wound-in defect(s) that later "grows" as multiple successive windings layers of the film are wound on top of the defect(s). These winding-induced defects can include: variations in print repeat length, tin can-type defects (e.g., the film roll exhibits a series of raised annular bands so as to resemble the side of a tin can), and gauge band types of defects. In this regard, while efforts are made to precisely design and build the mechanical components of the winding device, for large film width winding applications (e.g., on the order of 1 meter, 1.5 meters or even 2 meters or greater), unavoidable precision runouts tend to produce non-uniform tension during winding; in instances where the affected film layer is unable to readily move (or relax) relative to the immediately underlying layer (e.g., due to friction), one or more of the winding-induced defects mentioned above can occur. Winding defects are typically more frequently observed when the film is thin, has a low basis weight, and/or has a low modulus. In an embodiment, the film is has a thickness of ≤1 mm; preferably it is ≤0.75 mm. In an embodiment, the film has a basis weight of ≤20 gsm; preferably ≤16 gsm. In an embodiment, the film has a modulus of ≤20 N/cm; preferably about 16 N/cm. In an embodiment, the film is has a thickness of ≤1 mm, a basis weight of ≤20 gsm, and a modulus of ≤20 N/cm. In yet another embodiment, the film is has a thickness of ≤0.75 mm, a basis weight of ≤16 gsm, and a modulus of 16 N/cm.

The difference between the colors (i.e. ΔE) can be used to compare the colors graphic being printed versus target, e.g. when conducting test prints. In one embodiment, the ΔE between the graphic design fields is less than 16, but greater than 2. In another embodiment, the ΔE between the graphic being printed and the original design is less than 12, but greater than 4. In yet another embodiment, the ΔE between the graphic being printed and the original design is less than 9, but greater than 5.

Colors may be printed by using a variety of methods. Some suitable methods are single spot color; 4-color process printing (using cyan, magenta, yellow, and black; also known as "CMYK"); expanded color gamut 6-color or 7-color (CMYK+orange, green, and violet; also known as "OGV"); or a combination of 4-color, 6 color, or 7 color process printing with spot color printing. In an embodiment, 7 color process printing is combined with spot color printing. Additional factors to consider in adjusting settings are the shape and layout of the graphic. This may also include color-to-color alignment. Yet another factor to consider in adjusting settings is ink adhesion, e.g. how well it resists rub-off and/or leaching.

In an embodiment, the graphic is printed using a flexographic press. The flexographic generally operates by transferring ink from a soft rubber transfer roller to an anilox roll; this roll is filled with billions of tiny cells. Once they are filled, a doctor blade is used to scrape away any excess ink from the surface of the roller; this meters the quantity of ink to reach the printing plate. Ink is spread evenly on the anilox rollers to transfer ink to the raised parts of the flexible printing plate. The printing plate is wrapped around a plate cylinder. The raised sections of a flexographic printing plate are coated with ink ready to be pressed on the material to be printed. An impression cylinder presses the substrate (film) to be printed against the printing plate. The raised sections of the printing plate transfer their ink coating to the material being printed. The ink is dried. Each ink color requires its own anilox inking rollers, plate and cylinder, and colors are printed one after the other on to the material as it passes through the press.

In an embodiment, the flexographic press has a color-to-color registration accuracy of ±0.04 mm. Such a press is the ASTRAFLEX®, available from Windmoeller & Hoelscher Corp. Accordingly, by using a flexographic press with such accuracy in color-to-color registration, graphics may be printed having very narrow lines as fine as ≤0.032 inch in width, preferably ≤0.020 inch. Also suitable are flexographic presses known as the NOVOFLEX® and VISTAFLEX® (both available from W&H).

Suitable printing plates are typically made from one or more photopolymers and are typically supplied in flat sheets of un-reacted polymer. They are then processed by specialist pre-press houses. The use of a higher quality plate at this point in the process will typically result in a higher quality print ultimately being printed. Raised areas of the plate transfer the ink. In an embodiment, the relief is up to and including 0.8 mm in height. In an embodiment, the total thickness of the plate is from 1.3 to 1.7 mm, preferably 1.5 mm. In various embodiments, the thickness of the plate is selected from 1.14 mm (0.045"), 1.70 mm (0.067"), 2.28 mm (0.090"), 2.54 mm (0.100"), 2.72 mm (0.107"), and 2.84 mm (0.112"). In an embodiment, the thickness of the plate is 1.70 mm (0.067") with a relief of 0.020 inch. In another embodiment, the thickness of the plate is 1.70 mm (0.067") with a relief of 0.025 inch.

The anilox and doctor blade meter an even amount of ink to the printing plate. The ink is held in the billions of anilox cells while the doctor blade runs over the surface of the anilox removing any excess ink. The anilox is typically manufactured from a ceramic compound whose hardness provides long life and is resistant to abrasion from the doctor blade. The anilox roll is manufactured to release a certain ink weight from the laser engraved cells, so the size of the cells and resolution are important to the color on the final printed image.

There are two main types of ink supply and doctoring system used in flexography. In open systems the anilox rotates in an open bath of ink and the doctor blade meters the ink just prior to the ink being transferred to the plate cylinder.

The Chamber system encloses the ink using two blades within a chamber. The retaining blade at the bottom acts as a seal while the doctor blade at the top performs the ink metering. The ink is pumped through the system to maintaining a constant supply of ink to the anilox surface. Advantageously, the closed doctoring system requires less ink to "charge" the system and there is no release of VOC's, as the system is contained.

In an embodiment, the flexographic printing press comprises from 2 to 10 stations. These include but are not limited to three main configurations, the central impression press, the in-line press, and the stack press.

A web passes around the central impression (CI) cylinder with each color being printed in turn. Inter-station driers are used to cure the inks between print stations to ensure wet on dry printing. An advantage of this type of press is that registration is excellent, as the web is held over the CI drum between print stations. There is less chance of the substrate being extended between the print stations. The press speed of central impression presses can generally be increased beyond that of the other press types.

The in line press is a combination of individual units with a small distance between the print heads. Each color is printed on the web fed substrate. Each color has an individual impression cylinder against which the plate is pressed. An advantage of the in line press is that other printing technologies (such as rotary screen or gravure) and additional colors/processes can be incorporated by simply adding another station. These machines often use UV inks which are dried between each print station.

When using flexographic printing, certain management of the surface energy of print tools and substrates and the surface tension of the inks can lead to unexpected results. The surface tension/energy of the components of the printing process are advantageously arranged such that it increases from the inks, to anilox, to plates, to substrates. In one embodiment, the difference in surface tension/energy between the inks and the substrates is from 10 to 14 dynes, preferably 12 dynes/cm.

A design will typically comprise various design elements of the absorbent article. Design elements may be physical features of the absorbent article, such as the overall outline, location of tabs, fasteners, borders, junctions of materials, stitching, and like elements. Design elements may also be either actual physical features of the absorbent article or elements that are not actual physical features but are to be printed on the absorbent article to make it appear that they are actual elements of the absorbent article, non-limiting examples of features that may fall within either or both of these groups include: printing borders, seams, pockets, zippers, zipper flaps, topstitching, embossment, quilting, buttons, bows, ribbons, straps, snaps, belt loops, suspenders, sales tags, etc.

A design may also be themed or exhibit an otherwise like group of colors and patterns and/or solid prints. In an embodiment, they may be selected from groups being categorized as being gender neutral, boy appropriate, or girl appropriate. In another embodiment, they may be selected from groups categorized as being sporty, outdoors, sophisticated, professional, casual, cute, sassy, feminine (e.g. quilted, paisley, curly cues, polka dots), fresh, seasonal (e.g. spring, summer, fall, winter), patriotic, weather/climatic (e.g. sunny, rainy, snowy), ethnic, soft tones, earth tones, pastels, rock 'n roll, western (e.g. cowboy/cowgirl), animal, plant, food, or industrial.

The hue difference represents the distance between two points within CIELab color space. The CIELab color space hue difference ($\Delta H$) for a first color ($L^*_1$, $a^*_1$, $b^*_1$) and a second color ($L^*_2$, $a^*_2$, $b^*_2$), is calculated according to the following formula: $\Delta H = \sqrt{(\Delta E)^2 - (\Delta C)^2 - (\Delta L^*)^2}$. Within said formula, $\Delta E$ is the CIELab color space total color difference between the two colors and is calculated as presented above. The $\Delta C$ is the CIELab color space chroma difference between the two colors and is calculated by: $\Delta C = \sqrt{a^{*2}_2 + b^{*2}_2} - \sqrt{a^{*2}_1 + b^{*2}_1}$. The $\Delta L^*$ is the difference in $L^*$ values between the two colors and is calculated by: $\Delta L^* = L^*_2 - L^*_1$.

In an embodiment, at least two visible surfaces (such as two design fields) each comprising an imparted color will have a CIELab color space hue difference from about 6 to about 4 in order to show contrast. In another embodiment, the difference will be from about 5 to about 3. In yet another embodiment, the difference will be from about 4 to about 2. The visible surfaces are analyzed according to the Test Method described below. Upon analysis, the inherent color of an element comprising a visible surface will yield $L^*$, $a^*$, and $b^*$ coordinates. Two elements are selected and the $L^*$, $a^*$, and $b^*$ values of the elements are inserted into the formula presented above to result in a hue difference.

Visible surfaces are tested in a dry state and at an ambient humidity of approximately 50%±2%. Reflectance color is measured using the Hunter Lab LabScan XE reflectance spectrophotometer obtained from Hunter Associates Laboratory of Reston, Va. The spectrophotometer is set to the CIELab color scale and with a D50 illumination. The Observer is set at 10° and the Mode is set at 45/0°. Area View is set to 0.125" and Port Size is set to 0.20" for films; Area View is set to 1.00" and Port Size is set to 1.20" for nonwovens and other materials. The spectrophotometer is calibrated prior to sample analysis utilizing the black and white reference tiles supplied from the vendor with the instrument. Calibration is done according to the manufacturer's instructions as set forth in LabScan XE User's Manual, Manual Version 1.1, August 2001, A60-1010-862. If cleaning is required of the reference tiles or samples, only tissues that do not contain embossing, lotion, or brighteners should be used (e.g., Puffs® tissue). Any sample point on the visible surface of the element containing the imparted color to be analyzed should be selected. Typically, sample points are selected so as to be close in perceived color. A single ply of the element is placed over the spectrophotometer's sample port. A single ply, as used within the test method, means that the visible surface of the element is not folded. Thus, a single ply of a visible surface may include the sampling of a laminate, which itself is comprised of more than one lamina. The sample point comprising the color to be analyzed must be larger than the sample port to ensure accurate measurements. A white tile, as supplied by the manufacturer, is placed behind the visible surface. The $L^*$, $a^*$, and $b^*$ values are read and recorded. The visible surface is removed and repositioned so that a minimum of six readings are obtained for the visible surface. If possible (e.g., the size of the imparted color on the element in question does not limit the ability to have six discretely different, non-overlapping sample points), each of the readings is to be performed at a substantially different region on the visible surface so that no two sample points overlap. If the size of the imparted color region requires overlapping of sample points, only six samples should be taken with the sample points selected to minimize overlap between any two sample points. The readings are averaged to yield the reported $L^*$, $a^*$, and $b^*$ values for a specified color on a visible surface of an element.

Coordination in the present invention may also contain commonly used color schemes which tend to harmonize or coordinate. That is, the first and second visual color characteristics may be selected to enhance the visual coordination in addition to having at least a first and second color as the first and second visual characteristics. Examples of these color schemes include, for example, monochromatic color, complementary colors, analogous colors, warm and cool colors, neutral colors, color contrast, tetradic color scheme, triad color scheme or other chord color schemes. Monochromatic color scheme uses one base color but varies the color tint, shade and/or tone. Complementary colors are colors which are opposite each other on a color wheel. Analogous colors are colors which are adjacent each other on the color wheel. Warm and cool color schemes use three colors, two of which are warm colors and one is cool color or two cool colors and one warm color. Warm colors are generally associated with fire and the sun, for example, red, yellow and orange and cool colors are generally associated with water the sky and foliage, for example green, blue and violet. Neutral color coordination includes using shades of black, white, gray and beige together. Color contrast scheme include using dark and light colors together. Tetradic is a four color scheme and a triad color scheme is a three color scheme, both of which are known to those skilled in the art. Any of these color schemes may be used in the present invention to help coordinate and harmonize two or more colors as the visual characteristics in the present invention.

Coordination may be created by providing a theme on the absorbent article that matches the theme embodied in an article of clothing and/or line of clothing. Non-limiting examples of themes include: sporty, outdoors, sophisticated, professional, casual, cute, sassy, feminine (e.g. quilted, paisley, curly cues, polka dots), fresh, seasonal (e.g. spring, summer, fall, winter), patriotic, weather/climatic (e.g. sunny, rainy, snowy), ethnic, soft tones, earth tones, pastels, rock 'n roll, western (e.g. cowboy/cowgirl), animal, plant, food, or industrial.

Two patterns are considered coordinated when they have substantially the same pattern elements, regardless of other factors such as orientation.

In one embodiment, there are at least two different types of visual characteristics. One particular combination is the use of color and pattern. As set forth above, the more shared visual characteristics there are, the more coordinated the absorbent article and article of clothing and/or line of clothing will appear.

In various embodiments, the first visual characteristic may be a color and the second visual characteristic may be different colors embodied in an article of clothing and/or a line of clothing, with both of the colors applied to the absorbent article. In another embodiment, the first visual characteristic may be a color, and the second visual characteristic may be an embossment, pattern, or shape (e.g., fastening element). In yet another embodiment, the first visual characteristic may be a first embossment, printing or dyeing pattern and the second visual characteristic may be a second embossment, printing or dyeing pattern.

Embossing is an effective way to impart texture and pattern visual characteristics to an absorbent article. The embossing pattern may be a high density embossing pattern, or a low density embossing pattern, both of which may be registered or non-registered.

Additional examples of visual characteristics include: the location and appearance of tabs, fasteners, borders, junctions of materials, stitching, printing borders, seams, pockets, zippers, zipper flaps, topstitching, embossment, quilting, buttons, bows, ribbons, straps, snaps, belt loops, suspenders, and the like.

Further regarding seam, it may be desirable to color nonwovens such that the seams of the nonwoven where components are joined together result as darker. This may be accomplished by overlapping materials, such as where nonwoven belts are joined to form a seam or where the center chassis overlaps and is joined to nonwoven belts. This may also be accomplished by the overlap of discrete side panels being joined to the center chassis. Additionally or alternatively, a portion of the absorbent assembly may be colored such that it is visually distinct when viewed through the outer nonwovens and/or films of the center chassis. For example, a surge layer may be highly saturated with a color that is noticeable against a white film and white nonwovens making up the center chassis backsheet. In this example, the $\Delta H$ and/or $\Delta E$ may be different for the surge layer area versus the surrounding white areas around the surge layer area.

Graphics

Graphics comprise visual characteristics. Graphics, of course, may be printed in the manner described. And, as said above, graphics may be used to form design elements.

The belts 84 and 86 may comprise graphics 46a-i, including graphic objects and graphic patterns as disclosed in U.S. Publication Nos. 2011/0203102 and 2011/0192010, such that graphics 46 may form the appearance of a waistband around the entire, or substantially the entire, belt 40 as illustrated in FIGS. 1, 2 and 6. Further, the graphics of the present disclosure may be printed in the same manner as described in U.S. Publication Nos. 2011/0203102 and 2011/0192010, and may be printed on the exterior surface 22 of the article 20, or may be printed on an interior surface of the outer belt layer 82, or may be printed on the garment-facing surface of the inner belt 83, or may be printed on a discrete sheet (not shown) placed between the belt layers 82, 83. Further, the articles 20 disclosed herein may have graphics in accordance with U.S. Ser. Nos. 61/646,953 and 61/646,979, each filed on May 15, 2012.

Graphics 46a and b may be disposed on the front and rear regions 26, 28 and may cooperate to form two graphic fields that are coordinated or are the same pattern, or are substantially the same pattern. As shown in FIGS. 1, 2, and 6, the graphics 46a and 46b may each increase in longitudinal distance as they approach the longitudinal centerline L. For instance, as shown in FIG. 6, a graphic waistband may have a longitudinal distance 116 adjacent to the side seam, but may have a distance 118, which is greater than 116, at or near the longitudinal centerline L. In this way, the graphics 46a and 46b may taper as it nears the side seams 32a and b, or the side edges 47a and b of the front belt 84 and side edges 49a and b of the rear belt 86. This may give the appearance of a better fitting article, and may be especially advantageous when disposed on an article designed to fit under the wearer's bellybutton. Graphic designs that may be desirable for articles 20 of the present disclosure may have a longitudinal distance 116 adjacent the side edge 47 greater than about 15 mm, 25 mm, 50 mm, or about 75 mm, and may have a longitudinal distance 118, that is greater than the distance 116 at the side edge 47, but less than about 150 mm, 100 mm, or about 75 mm, including ranges in any combination of these.

Further, as shown in FIG. 6, the most longitudinally distal point adjacent the side seam 110 to the most longitudinally distal point 112 of a front or back graphic 46a or b may have an angle C that is at least about 110°, 120°, or about 130°, but not more than about 140°, relative to the longitudinal axis L. Alternatively, the back graphic 46b may be generally parallel with the transverse axis T. While FIG. 6 illustrates a graphic 46b that is generally parallel with the transverse axis T, graphic 46b may be replaced with a tapering graphic like the graphic 46a on the front belt 84, such that both graphics 46a and 46b on the front and back belts 84 and 86 are tapering graphics and such that the longitudinal distances 116 and 120 of the side edges 47 and 49 are about the same such that they may line up with each other.

The graphics 46a and b may be disposed into the seam 32, or to the very edge of the side edges 47, 49, or may stop outside of the seam 32.

A portion of the graphic 46a' of the front belt 84 may comprise an element that anchors the front belt 84 graphic 46a, such as a bow, or a knot. For example, the front belt 84 graphic 46a may be in the form of the appearance of lace, while the anchoring element 46a' is the appearance of a bow. This would be an example of a feminine graphic that functions to communicate a low cut panty and that may function to persuade the eye to see more of an extreme low cut feature (i.e., bikini-like underwear look) than there really is. In an alternative embodiment, the areas defined by 46a and b may be transparent, semi-transparent, or translucent instead of comprising a graphic. Further, in such an alternative embodiment, the transparent, semi-transparent, or translucent material may be partially printed or embossed with a graphic, such as the appearance of lace.

Further, the leg cuffs 64 may be colored or may comprise a graphic 46c and d that cooperates with the front belt 84 and/or back belt 86 graphics 46a, b, and c. This is especially beneficial in embodiments like illustrated in FIGS. 5B, 5C, and 7, where at least a portion of the leg cuffs 64 extends beyond the backsheet 60 or the nonwoven outer cover layer 42.

While graphics 46a-i may be printed to create graphic fields, one or more of graphics 46a-i may be textured and/or printed to create a graphic field. A graphic field or design field is an area that has a consistent design (e.g., a dark paisley pattern on a lightly tinted nonwoven may define a design field). Two design fields may border each other to create a contrast. For instance, a dark paisley pattern on a lightly tinted nonwoven may border a nonwoven lightly tinted without a pattern to create a contrast between the two design fields. Further, a bolder dark line may be disposed between the two design fields to better define the design fields. The bolder dark line may also be used to create the appearance of a seam, or may be used to overlap an actual seam of absorbent article materials. Overlapping the actual seam may be desirable for defining the design fields, as well as making the actual seam less noticeable, such that the seam has a lower Seam Noticeability Rating as described in U.S. Pat. No. 7,896,858. In the event that both design fields are saturated with a lot of color, it may be desirable to use a bold white line to separate the two design fields.

Further, one or more graphic fields may be formed by gathering the nonwoven in a manner that creates a distinct field. For example, bonding/gathering as described in U.S. Ser. Nos. 61/647,071 and 61/647,061 may be desirable to create one or more distinct graphic fields.

The following embodiments (E1-7) may be desirable:

Odor Control Agents

Absorbent articles 20 of the present disclosure may also comprise odor control agents, including reactive aldehydes, and including the compositions disclosed in PCT/US2014/042892 having an international filing date of Jun. 18, 2014. These agents may be disposed within the core 62, or on the topsheet 58 (including the garment-facing surface of the topsheet), or on the backsheet film 60 (including the body-facing surface of the backsheet).

Refastenable

The front and back belts 84 and 86 may be permanently or refastenably connected at the seams 32. Regarding refastenable embodiments, articles 20 of the present disclosure may have refastenable elements, configurations, and methods of making as disclosed in U.S. Ser. Nos. 61/787,416, filed on Mar. 15, 2013, as well as U.S. Ser. No. 61/787,332, filed on Mar. 15, 2013. The refastenable elements may be fastened during the manufacturing process and/or fastened in the package prior to use by the wearer or caregiver (i.e., the article may be sold in "closed form"). The front and back belts 84 and 86 may be in a number of configurations as described and illustrated in FIGS. 3A-C and 4A-k of U.S. Ser. No. 61/666,065, filed on Jun. 29, 2012, titled DISPOSABLE ABSORBENT Refastenable Pants and Methods for Manufacturing the Same.

Further, the absorbent articles of this disclosure may be manufactured in accordance with the descriptions and illustrations of U.S. Ser. No. 61/666,065 (see, for example, FIGS. 5-10C of the '065 application).

As illustrated, the belt 40 may be ring-like and elastic. The ring-like elastic belt 40 extends transversely about the waist opening 36 of the absorbent article 20 and acts to dynamically create and distribute forces dynamically generated during wear. Applicants have found that improved fit can be created by controlling the distance between, linear density, and the pre-strain of the elastomeric material in relation to each other and to the openings for the body. This may occur by choosing different materials throughout the belt 40 that exhibit desired properties. The different materials are combined at specific distances, linear densities, and prestrains to create a belt 40 that acts dynamically. Particularly, the articles 20 of this disclosure may have the characteristics of the articles of Examples 1-4 as disclosed in U.S. Ser. No. 13/764,990, filed Feb. 12, 2013. Articles of the present disclosure may also have the same stress, strain and spacing of its elastics as disclosed in U.S. Ser. No. 13/764,990 and/or as disclosed in U.S. Ser. No. 61/598,012, filed Feb. 13, 2012. Articles 20 of the present disclosure may also have the same elastic sections and force zones disclosed in U.S. Ser. No. 13/764,990.

TABLE 1

|    | Graphic 46a | Graphic 46b | Graphic 46c | Graphic 46d | Graphic 46e | Graphic 46f | Graphic 46g | Graphic 46h | Graphic 46i | Graphic 46j |
|----|-------------|-------------|-------------|-------------|-------------|-------------|-------------|-------------|-------------|-------------|
| E1 | Pattern A | Pattern A | Pattern B | Pattern B | Pattern C | Pattern C | Pattern D | Pattern E | Pattern F | Pattern F |
| E2 | Color field A | Color field A | Pattern A | Pattern A | Pattern B | Pattern B | Pattern C | Pattern D | Pattern E | Pattern E |
| E3 | Pattern A | Pattern A | Pattern B | Pattern B | Color field A | Color field A | Pattern C | Color field A | Pattern D | Pattern D |
| E4 | Pattern A | Pattern A | Pattern B | Pattern B | Color field A | Color field A | Pattern C | Color field B | Pattern D | Pattern D |

Note:
Different lettered patterns are different patterns and the same lettered patterns are the same patterns - the same is true for color fields. A color field has not pattern.

The belt 40 of this disclosure may comprise elasticized sections having the elastic profile combinations as disclosed in U.S. Pub. No. 2013/0211363, filed on Feb. 12, 2013, including elastic spacing, dtex, strains, border areas, spacer placement, force zones, force profiles, numbers of elastics, gap distance between the elastic strands, and the articles of the present disclosure may particularly have the elastic profiles as disclosed in Examples 1, 2, and 3 of U.S. Pub. No. 2013/0211363.

Further, the elasticized belts may be in a number of configurations as described and illustrated in FIGS. 3A-C and 4A-K of U.S. Pub. No. 2014/0005628, filed on Jun. 28, 2013, titled DISPOSABLE ABSORBENT REFASTENABLE PANTS AND METHODS FOR MANUFACTURING THE SAME. Further, the absorbent articles of this disclosure may be manufactured in accordance with the descriptions and illustrations of U.S. Pub. No. 2014/0005628 (see, for example, FIGS. 5-10C of the '628 publication).

It may be desirable to use the hot air seaming processes, as well as the article forming processes disclosed in U.S. Pat. No. 6,248,195 and U.S. Ser. Nos. 12/795,021, 13/401,907, and 13/402,056 for seaming articles as disclosed herein.

The articles 20 of the present disclosure may have Leg Hoop Moduluses, Leg Hoop Forces, and Array Leg Hoop Moduluses as disclosed in U.S. Ser. No. 61/976,668, filed Apr. 8, 2014, titled Array of Disposable Absorbent Articles For Fitting Broad Range Of Wearers, including the particular moduluses disclosed in Tables 1-4 of the '668 application.

Absorbent articles as disclosed herein may be manufactured by the same company on the same or different manufacturing line(s) and may sold in an array under the same brand (e.g., Pampers, Huggies, Depends, Always) and/or sub-brand name (Cruisers, Swaddlers, and Easy Ups, Baby Dry, Silhouette, etc.).

Identical or Substantially Identical Chassis

As disclosed in U.S. Pub. No. 2013-0211355, it may be desirable to offer an array of packages for fitting different sized wearers, but comprising identical or substantially identical chassis. For instance, an array may comprise a first package comprising a first size of absorbent articles 20 and a second package may comprise a second size of absorbent articles 20, where the first and second packages comprise identical or substantially identical center chassis 38 as described in U.S. Pub. No. 2013-0211355. More particularly, the first package may comprise a first center chassis 38 and the second package may comprise a second center chassis 38, where each of the first and second center chassis 38 comprise the same dimensions of one or more of: core width at the lateral centerline, core width at one of the front or rear core end, a distance from a left outer cuff distal edge to a right outer cuff distal edge, a distance from a left inner cuff distal edge to a left outer cuff distal edge, a distance from a left inner cuff proximal edge to a right inner cuff proximal edge, a distance from a left inner cuff proximal edge to a left outer cuff distal edge, a free height of the inner cuff, inner cuff hem fold width, inner cuff elastics length, outer cuff elastics length, core length, and backsheet width, as disclosed in U.S. Pub. No. 2013-0211355.

Further, each of the first and second chassis 38 may comprise identical chemical compositions of one or more of a topsheet 58, backsheet film 60, backsheet nonwoven 42, core super absorbent polymers, core pulp, core nonwoven, core tissue, leg cuff film, leg cuff nonwoven, super absorbent polymer adhesive, core nonwoven adhesive, leg cuff elastic adhesive, and backsheet nonwoven/film adhesive.

And, each of the first and second chassis 38 may comprise the same basis weight of one or more of the topsheet, backsheet film, backsheet nonwoven, core super absorbent polymers, core pulp, leg cuff nonwoven, leg cuff film, super absorbent polymer adhesive, leg cuff adhesive, and backsheet nonwoven/film adhesive.

And, each of the first and second chassis 38 may comprise compositionally identical core super absorbent polymers. The first and second chassis 38 may have identical component cross sectional order and disposition in at least one of the front region 26, back region 28, and crotch region 30. The leg cuffs 64 of the first and second chassis 38 may be composed of the compositionally identical materials.

And, the core adhesives of the first and second chassis 38 may be the same adhesive(s). The first and second chassis 38 may comprise core super absorbent polymers that are in the same chemical class and subclass.

And, each of the first and second chassis 38 may comprise first and second wetness indicators, respectively, and wherein the first and second wetness indicators are compositionally identical. The wetness indicators may be one color pre insult and a different color post insult. The wetness indicator may be appearing or disappearing graphics, such that a graphic object appears or disappears upon insult. Examples of suitable wetness indicators are disclosed in U.S. Pub. No. 2010/0262099.

Further, the leg cuffs 64 of the first and second chassis 38 may have identical component cross sectional order and disposition in at least one of the front waist region 26, back waist region 28, and crotch region 30. The distance from the left outer cuff distal edge to a right outer cuff distal edge may be the same. The distance from the left inner cuff proximal edge to left outer cuff distal edge may be the same. In some embodiments, the distance from the left inner cuff proximal edge to the right inner cuff proximal edge is the same. In some embodiments, the lengths of the inner and outer cuffs are the same.

In some embodiments, different size offerings in an array may have identical or substantially identical chassis as the flaps or belts may be used to enable the absorbent article to fit different sized wearers. For example, first and second absorbent articles may have identical chassis (compositionally, dimensionally, cross-sectionally), but the first article may have a different length due to disposition of the belts, such that the first article may be targeted to fit a smaller (in height, weight, or waist circumference) wearer than the second article. As a second example, first and second absorbent articles may have identical chassis (compositionally, dimensionally, cross-sectionally), but the first article may have a different length and/or width due to the size of the belts, such that the first article may be targeted to fit a smaller wearer than the second article.

In some embodiments, first and second absorbent articles may have identical chassis compositionally, but not dimensionally, and not cross-sectionally. In some embodiments, first and second absorbent articles may have identical chassis dimensionally, but not compositionally, and not cross-sectionally. In some embodiments, first and second absorbent articles may have identical chassis cross-sectionally, but not dimensionally, and not compositionally. In still other embodiments, first and second absorbent articles may have two, but not three of (1) compositionally, (2) dimensionally, and (3) cross-sectionally identical chassis.

Packages

The absorbent articles of the present disclosure may be placed into packages. The packages may comprise polymeric films and/or other materials. Graphics and/or indicia relating to properties of the absorbent articles may be formed on, printed on, positioned on, and/or placed on outer portions of the packages. Each package may comprise a plurality of absorbent articles. The absorbent articles may be packed under compression so as to reduce the size of the packages, while still providing an adequate amount of absorbent articles per package. By packaging the absorbent articles under compression, caregivers can easily handle and store the packages, while also providing distribution savings to manufacturers owing to the size of the packages.

Accordingly, packages of the absorbent articles of the present disclosure may have an In-Bag Stack Height of less than about 100 mm, less than about 95 mm, less than about 90 mm, less than about 85 mm, less than about 85 mm, but greater than about 75 mm, less than about 80 mm, less than about 78 mm, less than about 76 mm, or less than about 74 mm, specifically reciting all 0.1 mm increments within the specified ranges and all ranges formed therein or thereby, according to the In-Bag Stack Height Test described herein. Alternatively, packages of the absorbent articles of the present disclosure may have an In-Bag Stack Height of from about 70 mm to about 100 mm, from about 70 mm to about 95 mm, from about 72 mm to about 85 mm, from about 72 mm to about 80 mm, or from about 74 mm to about 78 mm, specifically reciting all 0.1 mm increments within the specified ranges and all ranges formed therein or thereby, according to the In-Back Stack Height Test described herein.

Figure 9:
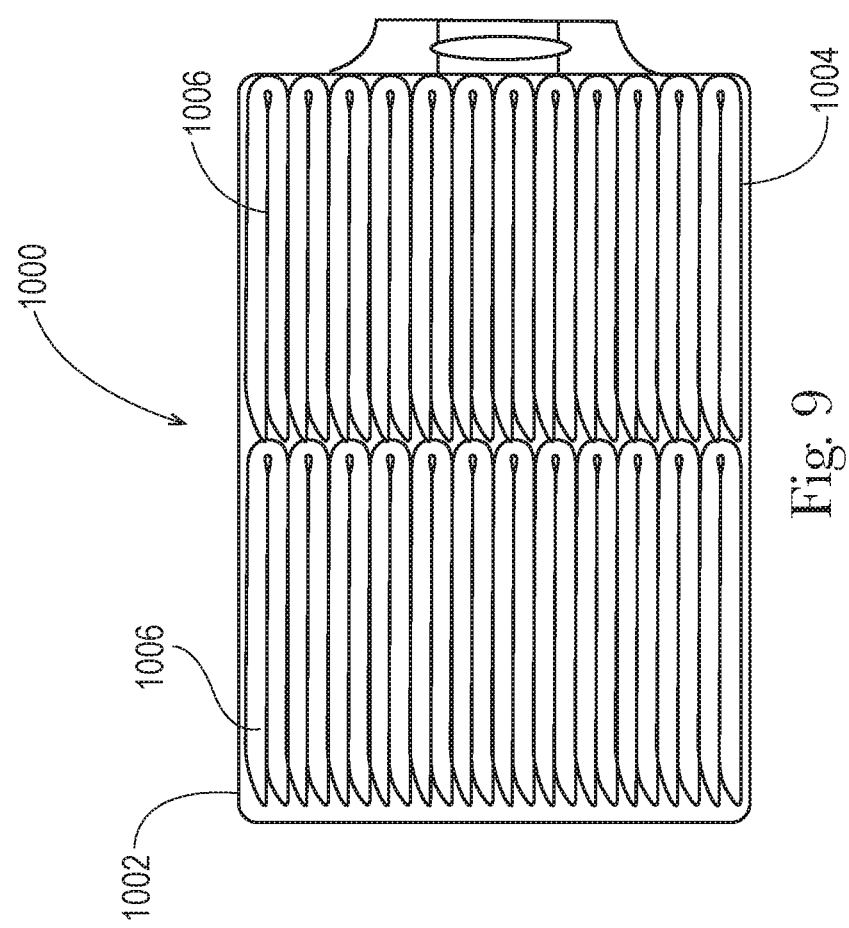
FIG. 9 is a schematic cross section view of suitable package of absorbent articles of the present disclosure.

FIG. 9 illustrates an example package 1000 comprising a plurality of absorbent articles 1004. The package 1000 defines an interior space 1002 in which the plurality of absorbent articles 1004 are situated. The plurality of absorbent articles 1004 are arranged in one or more stacks 1006.

In-Bag Stack Height Test

The in-bag stack height of a package of absorbent articles is determined as follows:

Equipment

A thickness tester with a flat, rigid horizontal sliding plate is used. The thickness tester is configured so that the horizontal sliding plate moves freely in a vertical direction with the horizontal sliding plate always maintained in a horizontal orientation directly above a flat, rigid horizontal base plate. The thickness tester includes a suitable device for measuring the gap between the horizontal sliding plate and the horizontal base plate to within ±0.5 mm. The horizontal sliding plate and the horizontal base plate are larger than the surface of the absorbent article package that contacts each plate, i.e. each plate extends past the contact surface of the absorbent article package in all directions. The horizontal sliding plate exerts a downward force of 850±1 gram-force (8.34 N) on the absorbent article package, which may be achieved by placing a suitable weight on the center of the non-package-contacting top surface of the horizontal sliding plate so that the total mass of the sliding plate plus added weight is 850±1 grams.

Test Procedure

Absorbent article packages are equilibrated at 23±2° C. and 50±5% relative humidity prior to measurement.

The horizontal sliding plate is raised and an absorbent article package is placed centrally under the horizontal sliding plate in such a way that the absorbent articles within the package are in a horizontal orientation (see FIG. 9). Any handle or other packaging feature on the surfaces of the package that would contact either of the plates is folded flat against the surface of the package so as to minimize their impact on the measurement. The horizontal sliding plate is lowered slowly until it contacts the top surface of the package and then released. The gap between the horizontal plates is measured to within ±0.5 mm ten seconds after releasing the horizontal sliding plate. Five identical packages (same size packages and same absorbent articles counts) are measured and the arithmetic mean is reported as the package width. The "In-Bag Stack Height"=(package width/absorbent article count per stack)×10 is calculated and reported to within ±0.5 mm.

Example Arrays

Further, absorbent article arrays of the present disclosure may be offered in Arrays 1-4, which are non-limiting examples, to accomplish the objects outlined in this application:

TABLE 2

ARRAY 1 (Inventive)

| | Front Belt width (mm) (124) | Back Belt width (mm) (126) | Front Belt Length (mm) (26) | Back Belt Length (mm) (28) | Product Rise (mm) (122) | Insert Length (mm) (128) | Insert Placement (mm) (130) | Number of Elastics in the Front Region | Number of Elastics in the Back Region |
|---|---|---|---|---|---|---|---|---|---|
| Article 1 | 648 | 648 | 179 | 193 | 658 | 471 | 70 | 27 | 33 |
| Article 2 | 728 | 728 | 196 | 213 | 752 | 471 | 117 | 29 | 39 |
| Article 3 | 808 | 808 | 219 | 238 | 860 | 471 | 171 | 32 | 46 |
| Article 4 | 648 | 648 | 200 | 214 | 700 | 548 | 52 | 30 | 36 |
| Article 5 | 728 | 728 | 211 | 227 | 780 | 548 | 92 | 31 | 41 |
| Article 6 | 808 | 808 | 219 | 238 | 860 | 548 | 132 | 32 | 46 |

TABLE 3

ARRAY 1 - Continued (Inventive)

| | Belt length (26 or 28) to Belt width (124 or 126) Ratio | Belt Length (26 or 28) to Insert Placement (130) Ratio | Insert Placement (130) to Belt Width (124 or 126) Ratio | Product Rise (122) to Belt Length (26 or 28) Ratio | Insert Placement (130) to Product Rise (122) Ratio | Insert Length (128) to Product Rise (122) Ratio |
|---|---|---|---|---|---|---|
| Article 1 | 0.28 | 2.56 | 0.11 | 0.39 | 0.11 | 0.72 |
| Article 2 | 0.27 | 1.68 | 0.16 | 0.60 | 0.16 | 0.63 |
| Article 3 | 0.27 | 1.28 | 0.21 | 0.78 | 0.20 | 0.55 |
| Article 4 | 0.31 | 3.85 | 0.08 | 0.26 | 0.07 | 0.78 |

TABLE 3-continued

ARRAY 1 - Continued (Inventive)

|  | Belt length (26 or 28) to Belt width (124 or 126) Ratio | Belt Length (26 or 28) to Insert Placement (130) Ratio | Insert Placement (130) to Belt Width (124 or 126) Ratio | Product Rise (122) to Belt Length (26 or 28) Ratio | Insert Placement (130) to Product Rise (122) Ratio | Insert Length (128) to Product Rise (122) Ratio |
|---|---|---|---|---|---|---|
| Article 5 | 0.29 | 2.29 | 0.13 | 0.44 | 0.12 | 0.70 |
| Article 6 | 0.27 | 1.66 | 0.16 | 0.60 | 0.15 | 0.64 |

In one embodiment, each of the articles from Array 1 may have the graphic arrangement as disclosed in Embodiment 1 (E1) of Table 1. Alternatively, Articles 1-3 may have the graphic arrangement as disclosed in Embodiment 1 (E1) of Table 1, while Articles 4-6 have the graphic arrangement as disclosed in Embodiment 2 (E2) of Table 1. Alternatively, at least 1 of Articles 1-6 may have the graphic arrangement as disclosed in Embodiment 1-6 (E1-6) of Table 1, while at least one of the Articles 1-6 may have the graphic arrangement as disclosed in one of the other embodiments of Table 1.

TABLE 4

ARRAY 2 (Inventive)

|  | Front Belt width (mm) (124) | Back Belt width (mm) (126) | Front Belt Length (mm) (26) | Back Belt Length (mm) (28) | Product Rise (mm) (122) | Insert Length (mm) (128) | Insert Placement (mm) (130) | Number of Elastics in the Front Region | Number of Elastics in the Back Region |
|---|---|---|---|---|---|---|---|---|---|
| Article 1 | 645-655 | 645-655 | 175-185 | 190-200 | 650-660 | 465-475 | 65-75 | 25-32 | 30-35 |
| Article 2 | 725-735 | 725-735 | 190-200 | 210-220 | 750-760 | 465-475 | 110-120 | 27-32 | 37-42 |
| Article 3 | 805-815 | 805-815 | 215-225 | 235-245 | 855-865 | 465-475 | 165-175 | 30-35 | 44-49 |
| Article 4 | 645-655 | 645-655 | 195-205 | 210-220 | 695-705 | 545-555 | 45-55 | 28-33 | 34-39 |
| Article 5 | 725-735 | 725-735 | 205-215 | 225-235 | 775-785 | 545-555 | 85-95 | 29-34 | 38-42 |
| Article 6 | 805-815 | 805-815 | 215-225 | 235-245 | 855-865 | 545-555 | 125-135 | 29-34 | 43-48 |

In one embodiment, each of the articles from Array 2 may have the graphic arrangement as disclosed in Embodiment 2 (E2) of Table 1. Alternatively, Articles 1-3 may have the graphic arrangement as disclosed in Embodiment 1 (E2) of Table 1, while Articles 4-6 have the graphic arrangement as disclosed in Embodiment 2 (E3) of Table 1. Alternatively, at least 1 of Articles 1-6 may have the graphic arrangement as disclosed in Embodiment 1-6 (E1-6) of Table 1, while at least one of the Articles 1-6 may have the graphic arrangement as disclosed in one of the other embodiments of Table 1.

TABLE 5

ARRAY 3 Exemplary (Inventive)

|  | Front Belt width (mm) (124) | Back Belt width (mm) (126) | Front Belt Length (mm) (26) | Back Belt Length (mm) (28) | Product Rise (mm) (122) | Insert Length (mm) (128) | Insert Placement (mm) (130) | Number of Elastics in the Front Region | Number of Elastics in the Back Region |
|---|---|---|---|---|---|---|---|---|---|
| Article 1 | 650 | 650 | 158 | 172 | 616 | 470 | 44 | 22-26 | 28-32 |
| Article 2 | 730 | 730 | 175 | 192 | 710 | 470 | 96 | 24-28 | 34-38 |
| Article 3 | 650 | 650 | 138 | 152 | 576 | 430 | 44 | 18-22 | 24-28 |
| Article 4 | 730 | 730 | 155 | 172 | 670 | 430 | 96 | 22-24 | 32-36 |

TABLE 6

ARRAY 3 - Continued (Inventive)

|  | Belt length (26 or 28) to Belt width (124 or 126) Ratio | Belt Length (26 or 28) to Insert Placement (130) Ratio | Insert Placement (130) to Belt Width (124 or 126) Ratio | Product Rise (122) to Belt Length (26 or 28) Ratio | Insert Placement (130) to Product Rise (122) Ratio | Insert Length (128) to Product Rise (122) Ratio |
|---|---|---|---|---|---|---|
| Article 1 | 0.24 | 3.59 | 0.07 | 0.28 | 0.07 | 0.76 |
| Article 2 | 0.24 | 1.82 | 0.13 | 0.55 | 0.14 | 0.66 |

TABLE 6-continued

ARRAY 3 - Continued (Inventive)

| | Belt length (26 or 28) to Belt width (124 or 126) Ratio | Belt Length (26 or 28) to Insert Placement (130) Ratio | Insert Placement (130) to Belt Width (124 or 126) Ratio | Product Rise (122) to Belt Length (26 or 28) Ratio | Insert Placement (130) to Product Rise (122) Ratio | Insert Length (128) to Product Rise (122) Ratio |
|---|---|---|---|---|---|---|
| Article 3 | 0.21 | 3.14 | 0.07 | 0.32 | 0.08 | 0.75 |
| Article 4 | 0.21 | 1.61 | 0.13 | 0.62 | 0.14 | 0.64 |

In one embodiment, each of the articles from Array 3 may have the graphic arrangement as disclosed in Embodiment 3 (E3) of Table 1. Alternatively, Articles 1-3 may have the graphic arrangement as disclosed in Embodiment 3 (E3) of Table 1, while Articles 4-6 have the graphic arrangement as disclosed in Embodiment 4 (E4) of Table 1. Alternatively, at least 1 of Articles 1-6 may have the graphic arrangement as disclosed in Embodiment 1-6 (E1-6) of Table 1, while at least one of the Articles 1-6 may have the graphic arrangement as disclosed in one of the other embodiments of Table 1.

TABLE 7

ARRAY 4 (Inventive)

| | Front Belt width (mm) (124) | Back Belt width (mm) (126) | Front Belt Length (mm) (26) | Back Belt Length (mm) (28) | Product Rise (mm) (122) | Insert Length (mm) (128) | Insert Placement (mm) (130) | Number of Elastics in the Front Region | Number of Elastics in the Back Region |
|---|---|---|---|---|---|---|---|---|---|
| Article 1 | 650 | 650 | 180 | 195 | 655 | 470 | 70 | 25-32 | 30-35 |
| Article 2 | 730 | 730 | 195 | 215 | 755 | 470 | 115 | 27-32 | 37-42 |
| Article 3 | 810 | 810 | 220 | 240 | 860 | 470 | 170 | 30-35 | 44-49 |
| Article 4 | 650 | 650 | 200 | 215 | 700 | 550 | 50 | 28-33 | 34-39 |
| Article 5 | 730 | 730 | 210 | 230 | 780 | 550 | 90 | 29-34 | 38-42 |
| Article 6 | 810 | 810 | 220 | 240 | 860 | 550 | 130 | 29-34 | 43-48 |

TABLE 8

ARRAY 4 - Continued (Inventive)

| | Belt length (26 or 28) to Belt width (124 or 126) Ratio | Belt Length (26 or 28) to Insert Placement (130) Ratio | Insert Placement (130) to Belt Width (124 or 126) Ratio | Product Rise (122) to Belt Length (26 or 28) Ratio | Insert Placement (130) to Product Rise (122) Ratio | Insert Length (128) to Product Rise (122) Ratio |
|---|---|---|---|---|---|---|
| Article 1 | 0.28 | 2.57 | 0.11 | 0.39 | 0.11 | 0.72 |
| Article 2 | 0.27 | 1.70 | 0.16 | 0.59 | 0.15 | 0.62 |
| Article 3 | 0.27 | 1.29 | 0.21 | 0.77 | 0.20 | 0.55 |
| Article 4 | 0.31 | 4.00 | 0.08 | 0.25 | 0.07 | 0.79 |
| Article 5 | 0.29 | 2.33 | 0.12 | 0.43 | 0.12 | 0.71 |
| Article 6 | 0.27 | 1.69 | 0.16 | 0.59 | 0.15 | 0.64 |

In one embodiment, each of the articles from Array 4 may have the graphic arrangement as disclosed in Embodiment 4 (E2) of Table 1. Alternatively, Articles 1-3 may have the graphic arrangement as disclosed in Embodiment 4 (E4) of Table 1, while Articles 4-6 have the graphic arrangement as disclosed in Embodiment 5 (E5) of Table 1. Alternatively, at least 1 of Articles 1-6 may have the graphic arrangement as disclosed in Embodiment 1-6 (E1-6) of Table 1, while at least one of the Articles 1-6 may have the graphic arrangement as disclosed in one of the other embodiments of Table 1.

TABLE 9

| | \multicolumn{7}{c|}{ARRAY 5: Comparative (Non-Inventive, currently marketed)} |
|---|---|---|---|---|---|---|---|
| | Front Belt width (mm) (124) | Back Belt width (mm) (126) | Front Belt Length (mm) (26) | Back Belt Length (mm) (28) | Product Rise (mm) (122) | Insert Length (mm) (128) | Insert Placement (mm) (130) |
| Article 1 | 580 | 580 | 140 | 140 | 580 | 460 | 50 |
| Article 2 | 640 | 640 | 170 | 170 | 760 | 490 | 100 |

TABLE 10

| | ARRAY 5 - Continued: Comparative (Non-Inventive, currently marketed) | | | | | |
|---|---|---|---|---|---|---|
| | Belt length (26 or 28) to Belt width (124 or 126) Ratio | Belt Length (26 or 28) to Insert Placement (130) Ratio | Insert Placement (130) to Belt Width (124 or 126) Ratio | Product Rise (122) to Belt Length (26 or 28) Ratio | Insert Placement (130) to Product Rise (122) Ratio | Insert Length (128) to Product Rise (122) Ratio |
| Article 1 | 0.24 | 2.80 | 0.09 | 0.36 | 0.09 | 0.79 |
| Article 2 | 0.27 | 1.70 | 0.16 | 0.59 | 0.13 | 0.64 |

TABLE 11

| | ARRAY 6: Comparative (Non-Inventive, currently marketed) | | | | | |
|---|---|---|---|---|---|---|
| | Front Belt width (mm) (124) | Back Belt width (mm) (126) | Front Belt Length (mm) (26) | Back Belt Length (mm) (28) | Product Rise (mm) (122) | Insert Length (mm) (128) | Insert Placement (mm) (130) |
| Article 1 | 700 | 700 | 190 | 190 | 750 | 410 | 120 |
| Article 2 | 760 | 760 | 240 | 240 | 850 | 410 | 170 |
| Article 3 | 800 | 800 | 200 | 200 | 900 | 410 | 140 |

TABLE 12

| | ARRAY 6 - Continued: Comparative (Non-Inventive, currently marketed) | | | | | |
|---|---|---|---|---|---|---|
| | Belt length (26 or 28) to Belt width (124 or 126) Ratio | Belt Length (26 or 28) to Insert Placement (130) Ratio | Insert Placement (130) to Belt Width (124 or 126) Ratio | Product Rise (122) to Belt Length (26 or 28) Ratio | Insert Placement (130) to Product Rise (122) Ratio | Insert Length (128) to Product Rise (122) Ratio |
| Article 1 | 0.27 | 1.58 | 0.17 | 0.63 | 0.16 | 0.55 |
| Article 2 | 0.32 | 1.41 | 0.22 | 0.71 | 0.20 | 0.48 |
| Article 3 | 0.25 | 1.43 | 0.18 | 0.7 | 0.16 | 0.46 |

With regard to these arrays, it should be noted that the present disclosure reveals the importance of portion of the product rise (i.e., article length (122), also known as pitch) that is covered by the length of central chassis 38 (i.e., insert length (128)).

While elements of the present disclosure have been disclosed in the context of adult incontinence absorbent articles, these elements may also be applicable to use on an absorbent article for newborns, infants, or toddlers.

The dimensions and values disclosed herein are not to be understood as being strictly limited to the exact numeral values recited. Instead, unless otherwise specified, each such dimension is intended to mean both the recited value and a functionally equivalent range surrounding that value. For example, a dimension disclosed as "40 mm" is intended to mean "about 40 mm."

All documents cited in the Detailed Description of the Invention are, in relevant part, incorporated herein by reference; the citation of any document is not to be construed as an admission that it is prior art with respect to the present invention. To the extent that any meaning or definition of a term in this written document conflicts with any meaning or definition of the term in a document incorporated by reference, the meaning or definition assigned to the term in this written document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. An adult incontinence pant comprising:
a chassis comprising a topsheet, a backsheet, and an absorbent core;
a front belt in a front waist region and a back belt in a back waist region, the front belt and the back belt meeting to form first and second side seams, and a crotch region therebetween the front and back waist regions;
wherein the front belt extends continuously transversely across the front waist region of the absorbent article, and wherein the back belt extends continuously transversely across the back waist region of the absorbent article;
an outer nonwoven layer that is continuous from a front waist edge to a back waist edge;
wherein the front belt comprises the outer nonwoven layer and an inner nonwoven front belt layer;
wherein the back belt comprises the outer nonwoven layer and an inner nonwoven back belt layer;
wherein the inner nonwoven front belt layer is discrete and wherein the inner nonwoven back belt layer is discrete, such that the inner nonwoven front belt layer and the inner nonwoven back belt layer are not connected in the crotch region;
wherein the front belt comprises a first graphic field;
wherein at least a portion of the first graphic field is disposed adjacent to the front waist edge and is disposed adjacent to the first and second side seams;
wherein the first graphic field extends across the front waist region; and
wherein the first graphic field has a first longitudinal distance at or adjacent to the first side seam and a second longitudinal distance at or adjacent to a longitudinal axis of the absorbent article, and wherein the second longitudinal distance is greater than the first longitudinal distance and the first graphic field tapers.

2. The adult incontinence pant of claim 1, wherein the front belt comprises a first plurality of elastic strands between the outer nonwoven layer and the inner nonwoven front belt layer, wherein the first plurality of elastic strands extend continuously transversely across the front waist region; and
wherein the back belt comprises a second plurality of elastic strands between the outer nonwoven layer and the inner nonwoven back belt layer, wherein the second plurality of elastic strands extend continuously transversely across the back waist region.

3. The adult incontinence pant of claim 2, wherein the first plurality of elastic strands overlap the chassis.

4. The adult incontinence pant of claim 2, wherein the second plurality of elastic strands overlap the chassis.

5. The adult incontinence pant of claim 1, wherein the front and back belts comprise apertured films.

6. The adult incontinence pant of claim 1, wherein the front belt comprises a second graphic field.

7. The adult incontinence pant of claim 6, wherein the second graphic field is disposed to overlap with the longitudinal axis of the absorbent article.

8. The adult incontinence pant of claim 6, wherein the front belt comprises a plurality of elastic strands, and wherein the first and second graphic fields overlap the plurality of elastic strands.

9. The adult incontinence pant of claim 6, wherein the front belt comprises a film, and wherein the first and second graphic fields overlap the film.

10. The adult incontinence pant of claim 6, wherein the first and second graphic fields have different visual characteristics.

11. The adult incontinence pant of claim 6, wherein the second graphic field is an oval or is circular.

12. The adult incontinence pant of claim 6, wherein the first and second graphic fields appear to overlap.

13. The adult incontinence pant of claim 6, wherein the first graphic field is a different pattern than the second graphic field.

14. The adult incontinence pant of claim 6, wherein the first graphic field is a different shape than the second graphic field.

15. The adult incontinence pant of claim 6, wherein the second graphic field is disposed closer to a transverse axis of the absorbent article.

16. The adult incontinence pant of claim 6, wherein the back belt comprises a third graphic field having a first longitudinal distance at or adjacent to the first side seam and a second longitudinal distance at or adjacent to the longitudinal axis of the absorbent article, and wherein the first and second distances are different such that the third graphic field tapers.

17. The adult incontinence pant of claim 1, wherein the first graphic field forms an appearance of lace.

18. The adult incontinence pant of claim 1, wherein the first graphic field forms an appearance of a waistband.

19. The adult incontinence pant of claim 1, wherein the first graphic field extends adjacent to and along the front waist edge in the front waist region.

* * * * *